(12) United States Patent
Sato et al.

(10) Patent No.: US 6,320,069 B1
(45) Date of Patent: Nov. 20, 2001

(54) PRODUCTION OF OPTICALLY ACTIVE KETONE

(75) Inventors: Haruyo Sato, Nagoya; Sakie Nakai, Tokoname; Keiko Funabashi, Niwa; Shiho Iwata, Inazawa, all of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/202,793

(22) PCT Filed: Jul. 2, 1997

(86) PCT No.: PCT/JP97/02294

§ 371 Date: Dec. 22, 1998

§ 102(e) Date: Dec. 22, 1998

(87) PCT Pub. No.: WO98/00382

PCT Pub. Date: Jan. 8, 1998

(30) Foreign Application Priority Data

| Jul. 2, 1996 | (JP) | 8-172711 |
| Oct. 7, 1996 | (JP) | 8-266416 |
| Nov. 22, 1996 | (JP) | 8-312486 |
| Jan. 13, 1997 | (JP) | 9-004094 |

(51) Int. Cl.⁷ .................................................. C07C 69/00
(52) U.S. Cl. ..................... 560/130; 560/155; 560/231; 562/401; 562/433; 562/553; 562/585; 568/304; 568/338; 568/357
(58) Field of Search ..................... 560/130, 155, 560/231; 562/401, 433, 553, 585; 568/304, 338, 357

(56) References Cited

U.S. PATENT DOCUMENTS

| 3,528,965 | 9/1970 | Cole et al. . |
| 4,721,803 | * 1/1988 | Cesa et al. ............................ 560/41 |

FOREIGN PATENT DOCUMENTS

| 640 240 | 12/1983 | (CH) . |
| 0199257 | * 10/1986 | (EP) . |
| 0 339 751 | 4/1989 | (EP) . |
| 0 532 341 | 9/1992 | (EP) . |
| 1-100142 | * 4/1989 | (JP) . |
| 4-59742 | * 2/1992 | (JP) . |
| 5-279326 | * 10/1993 | (JP) . |
| 6-507940 | * 12/1993 | (JP) . |
| WO 97/22610 | 6/1997 | (WO) . |
| WO 98/02551 | 1/1998 | (WO) . |

OTHER PUBLICATIONS

Bell, Autralian J. Chem., 40, 399–404, 1987.*
International Search Report dated Aug. 17, 1998.

* cited by examiner

Primary Examiner—Sreeni Padmanabhan
(74) Attorney, Agent, or Firm—Schnader Harrison Segal & Lewis LLP

(57) ABSTRACT

Process for producing an optically active ester by reaction of a racemic alcohol with an optically active amino or tartaric acid derivative, a process for producing an optically active alcohol by hydrolysis of the optically active ester, a process for converting an alcohol into a ketone by oxidation, a method for stably storing an optically active ketone, and a new optically active amino acid ester and a new optically active tartaric acid ester.

54 Claims, 7 Drawing Sheets

PRODUCTION OF OPTICALLY ACTIVE KETONE

TECHNICAL FIELD

The present invention relates to a process for producing an optically active ketone which is an important intermediate for medicines and agricultural chemicals. More particularly, the present invention relates to a process for producing an optically active ester by reaction of a racemic alcohol with an optically active amino acid derivative or optically active tartaric acid derivative, to a process for producing an optically active alcohol by hydrolysis of said optically active ester, to a process for converting an alcohol into a ketone by oxidation, to a method for stably storing an optically active ketone, and to a new optically active amino acid ester and a new optically active tartaric acid ester.

BACKGROUND ART (1) Production of optically active alcohol: There have been known several processes for, production of optically active alcohols. For example, (1) symmetric hydrolysis of an carboxylate ester of racemic alcohol by an enzyme (Agric. Biol. Chem., 46, 757 (1982)); (2) asymmetric hydrogenation if a ketone as a precursor by an enzyme (Nippon Kagaku Zasshi, 1315 (1983)); and (3) asymmetric reduction of a ketone as a precursor by an asymmetric catalyst and hydrogen (J. Am. Chem. Soc., 101, 3129 (1979)). These processes are favorable to production of optically active alcohols but have their respective disadvantages. Process (1) needs an expensive enzyme and often involves difficulty in obtaining alcohols of high optical purity due to the enzyme's optical selectivity which greatly varies depending on the desired compound. Process (2) also needs an expensive enzyme and generally suffers the low enzymatic, activity. Process (3) needs an expensive asymmetric catalyst and involves difficulty in obtaining alcohols of high optical purity.

(2) Esterifying reaction: There have been known several processes for producing optically active alicyclic alcohol derivatives. For example, (1) reaction of a racemic cyclohexanol derivative with propionic acid (to give an ester), followed by enzymatic resolution by lipase (Synthesis 1137 (1990)); and (2) reaction of racemic alcohol with phthalic anhydride (to give a racemic carboxylic acid), followed by optical resolution by the aid of optically active α-phenylethylamine and subsequent hydrolysis to give an optically active alcohol (European Patent No. 656344). These processes are superior in production of optically active alicyclic alcohol derivatives but have their respective disadvantages. Process (1) needs an expensive enzyme and involves difficulty in obtaining alicyclic alcohol derivatives of high optical purity due to the enzyme's optical selectivity which greatly varies depending on the desired compound. Process (2) needs complex steps of synthesizing a phthalic acid derivative, forming a diastereomer salt with optically active α-phenylethylamine, and performing optical resolution.

(3) Oxidation of an alcohol to produce a ketone: There have been known several processes for producing an alicyclic ketone from in alicyclic alcohol by oxidation with a hypohalous acid. For example, (1) reaction of cycloheptanol with sodium hypochlorite in the presence of a quaternary ammonium salt (Tetrahedron Letter (1976), 2, 1641); (2) reaction a optically active menthol with sodium hypochlorite in glacial acetic acid (as a solvent) to give optically active menthone (J. Org. Chem., (1980), 45, 2030); (3) reaction of cycloalkanol with alkali metal (or alkaline earth metal) hypohalite at pH 6 or below in water and water-miscible solvent to give an alicyclic alcohol (Japanese Patent Laid-open No. 211629/1992); and (4) reaction of optically active 2-alkoxycyclohexanol with hypohalous acid or a source thereof to give an optically active 2-alkoxycycloalkanone (GB 2283971).

These processes have their respective disadvantages. Process (1) needs a quaternary ammonium salt (which adds to the production cost) and a complex step to separate the reaction product. Process (2) needs A complex step to separate the reaction product as the result of using glacial acetic acid as a solvent, although it efficiently yields the desired product without decrease in optical purity. Process (3) needs a complex step to separate the reaction product because of reaction in a water-miscible solvent. Process (4) gives rise to an undesirable by-product when the reaction is carried out in the presence of a ketone according to the most preferable embodiment. This by-product is a ketone with its α-position chlorinated. In the case where the ketone is acetone or methyl ethyl ketone, the by-product is α-chloroketone which is highly toxic to human bodies and possesses tearing properties. It aggravates the purity of the reaction product and has an adverse effect on the health of operators in the case of commercial production.

In addition, the optically active 2-alkoxycycloalkanone produced by the above-mentioned process decreases in chemical purity and undergoes racemization if it is stored at room temperature (about 30° C.) after purification by distillation. Although the optically active α-substituted cyclic ketone is unstable, nothing is known about the method of stabilizing it.

DISCLOSURE OF THE INVENTION

The present invention was completed to eliminate the above-mentioned disadvantages involved in the prior art technology. Accordingly, it is an object of the present invention to provide a process for reacting a racemic alcohol with an optically active amino acid derivative or tartaric acid derivative, thereby producing optically active esters, to provide a process for hydrolyzing them, thereby giving optically active alcohols, to provide a process for oxidizing the alcohols into ketones, to provide a method for stably storing the optically active ketones, and to provide a new optically active amino acid ester and tartaric acid ester.

BEST MODE FOR CARRYING OUT THE INVENTION

Synthesis of amino acid esters

Figure 1:
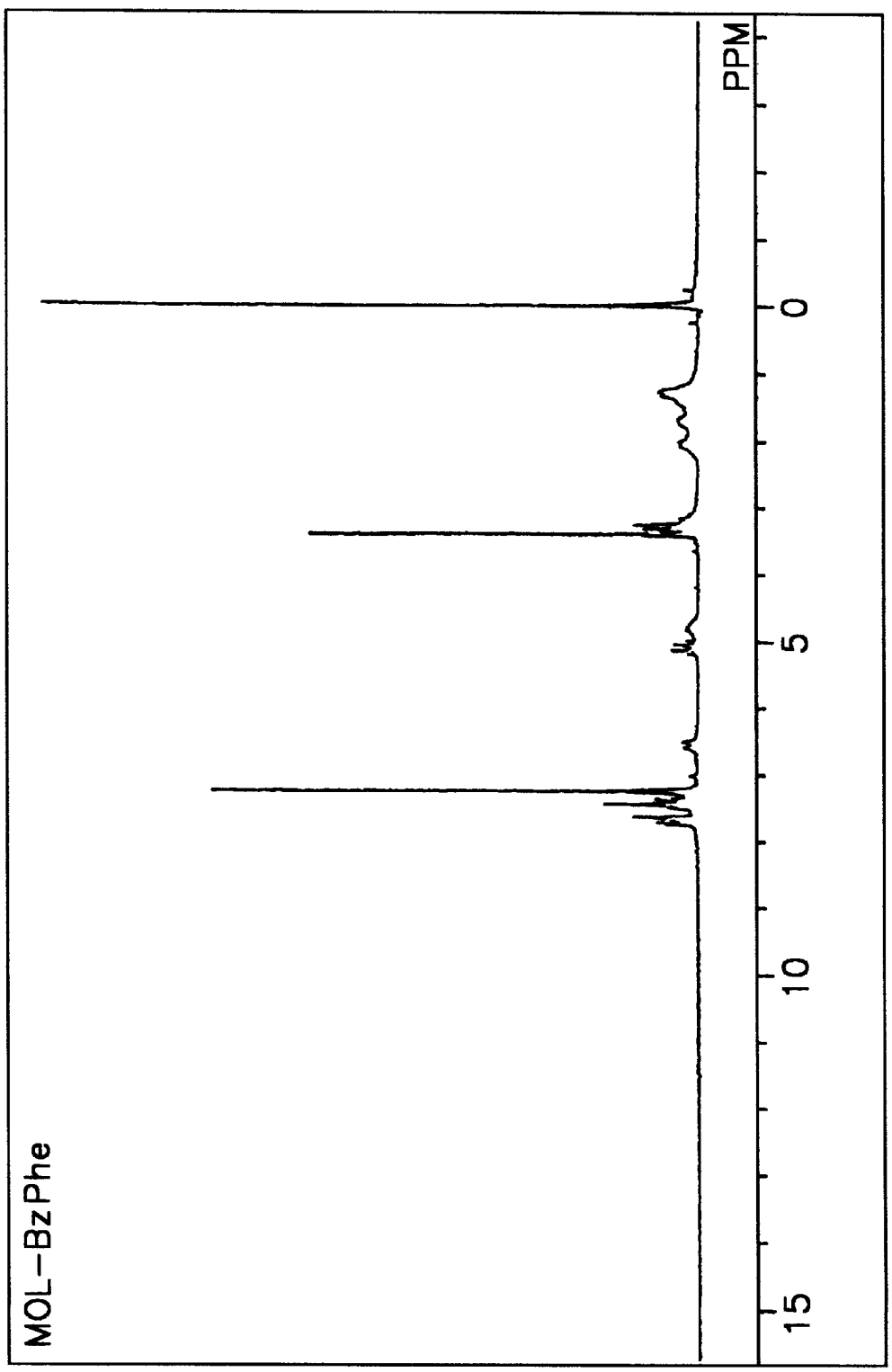
FIG. 1 is an NMR chart of (1S)-(N-benzoyl-L-phenylalanyloxy)-(2S)-methoxycyclohexane obtained in Example 1.

According to the present invention, amino acid esters are synthesized from racemic alcohols exemplified below.

alkyl secondary alcohols such as methylethyl alcohol.

aralkyl alcohols such as α-phenylethyl alcohol.

alicyclic alcohols such as 2-methoxycyclohexanol.

heterocyclic alcohols such as 1-ethyl-3-hydroxypyridine and N-benzyl-3-pyrrolidinol.

primary alcohols such as N-methyl-2-pyrrolidine ethanol.

diols such is 1-phenyl-1,3-propanediol.

In addition, racemic alcohols include not only a mixture of R-form and S-form in equal amounts but also a mixture containing S-form or R-form in an amount more than 50% and less than 99%.

The optically active amino acids used in the present invention may be either those of S-configuration or those of R-configuration depending on the intended use. Although natural L-α-amino acids are desirable because of their ready commercial availability at low prices, it is also possible to use non-natural amino acids. Examples of amino acids are shown below.

natural amino acids such as L-alanine, L-phenylalanine, L-proline, L-valine, L-isoleucine, and L-leucine.

non-natural amino acids such as D-alanine, D-phenylalanine, D-proline, D-valine, D-isoleucine, D-leucine, L-pyrrolidone-5-carboxylic acid, D-phenylglycine, D-pyrrolidone-5-carboxylic acid, and L-phenylglycine.

heterocyclic amino acids such as L-indoline-2-carboxylic acid and D-indoline-2-carboxylic acid.

These amino acids may be used as such or after conversion into an acyl derivative or sulfonyl derivative by N-substitution of the amino group in consideration of reactivity and resolution efficiency. Acyl derivatives of amino acids include, for example, those which are modified with any of alkylcarbonyl group (such as acetyl, propionyl, and butyroyl), arylcarbonyl group (such as benzoyl, toluoyl, and chlorobenzoyl), aralkylcarbonyl group (such as benzylcarbonyl, phenethylcarbonyl, and chlorobenzylcarbonyl), and benzyloxycarbonyl group. Sulfonyl derivatives of amino acids include, for example, those which are modified with any of alkylsulfonyl group (such as methanesulfonyl and ethanesulfonyl), arylsulfonyl group (such as benzenesulfonyl, toluenesulfonyl, and chlorobenzenesulfonyl), and aralkylsulfonyl group (such as benzylsulfonyl, phenethylsulfonyl, and chlorobenzylsulfonyl).

The ester of the optically active amino acid and racemic alcohol can be produced by the ordinary processes such as reacting the optically active amino acid (in the form of acid halide) with the racemic alcohol, reacting the optically active amino acid with the racemic alcohol in the presence of an esterifying catalyst, and reacting the optically active amino acid (in the form of acid anhydride) with the racemic alcohol.

(2) Synthesis of optically active tartaric acid ester

The tartaric a id ester in the present invention may be synthesized from an optically active tartaric acid derivative anhydride of either L-form or D-form, depending on the intended use. A natural L-tartaric acid derivative anhydride is desirable because of its ready availability at a low price, However, it is also possible to use a D-tartaric acid derivative anhydride Examples include O,O'-diacetyl-L-tartaric acid, O,O'-diacetyl-D-tartaric acid, O,O'-dibenzyl-L-tartaric acid, O,O'-benzyl-D-tartaric acid, O,O'-dibenzoyl-L-tartaric acid, O,O'-benzoyl-D-tartaric acid, O,O'-ditoluoyl-L-tartaric acid, O,O'-ditoluoyl-D-tartaric acid, O,O'-di(parachlorobenzoyl)-L-tartaric acid, O,O'-di(parachlorobenzoyl)-D-tartaric acid, O,O'-di(3,4-dimethylbenzoyl)-L-tartaric acid, O,O'-di(3-dimethylbenzoyl)-D-tartaric acid, O,O'-di(methoxybenzoyl)-L-tartaric acid, and O,O'-di(methoxybenzoyl)-D-tartaric acid.

The reaction between the optically active tartaric acid derivative anhydride and the racemic secondary alcohol is carried out in a solvent or in the presence of a Lewis acid without solvent. Examples of the Lewis acid include aluminum chloride, zinc chloride, and iron chloride, with the last being preferable from the standpoint of easy operation. It should be used in an amount of 0.01–20 mol %, preferably 0.1–10 mol %, of the amount of the racemic secondary alcohol derivative.

Solvents are not specifically restricted so long as they are not involved in the reaction. Preferred examples of solvents include aromatic hydrocarbons (such as benzene, toluene, and xylene) and alkyl halide (such as dichloromethane and chloroform).

The reaction temperature should be 0–150° C., preferably room temperature to 120° C. Reaction at low temperatures takes a long time and reaction at high temperatures gives rise to impurities.

The present invention permits easy synthesis of a tartrate ester from a racemic alcohol and an optically active tartaric acid derivative anhydride.

(3) Diastereomer resolution of optically active ester

According to the present invention, the optically active amino acid ester or tartaric acid ester prepared as mentioned above undergoes diastereomer resolution in the following manner. There are several ways for optical resolution. For example, separation by crystallization that utilizes a difference in solubility, separation by passage through a column, and separation by the aid of a quasi moving bed. Their selection depends on the desired product.

Crystallization employs as a solvent water, alcohols, aliphatic hydrocarbons, aromatic hydrocarbons, ketones, ethers, and mixtures thereof. Columns are filled with silica gel, modified silica gel, zeolite, alumina, or the like. Quasi moving beds are effective for column separation in commercial production. Developing solvents should be chemically stable. Their examples include aromatic hydrocarbons (such as benzene and toluene), halogenated hydrocarbons (such as dichloromethane and chloroform), alicyclic hydrocarbons (such as cyclohexane and cyclooctane), and acetonitrile. Their selection depends on the kind of the amino acid ester and tartaric acid ester and also on the filler used. They may be used alone or in combination with one another.

According to the present invention, a racemic alcohol an optically active amino acid or tartaric acid derivative anhydride are easily synthesized into an amino acid ester or tartaric acid ester, which is subsequently converted into an optically active tartaric acid ester of high optical purity by diastereomer resolution or into an optically active alicyclic alcohol derivative (which is an important intermediate for medicines) by hydrolysis.

(4) New optically active ester

The new optically active ester of the present invention is an optically active amino acid ester or tartaric acid ester which is obtained from an amino acid ester or tartaric acid ester by diastereomer resolution. Incidentally, the expression "optically active tartaric acid ester" implies a mixture of esters in which either the (S)-form or the (R) form of the alicyclic alcohol accounts for more than 80% of the total.

(5) Hydrolysis of optically active esters

According to the present invention, following diastereomer resolution, the optically active amino acid esters are hydrolyzed so as to produce the desired optically active alcohols. This hydrolysis may be accomplished by use of either acid or alkali; but it should be carried out such that the desired alcohols do not undergo racemization. This object is achieved by reaction with an aqueous solution of mineral acid (such as sulfuric acid, and hydrochloric acid) or an aqueous solution of alkali (such as sodium hydroxide, potassium hydroxide, sodium carbonate; and sodium hydrogen carbonate). Water as a medium may be used in combination with an organic solvent such as methanol, isopropanol, acetone, toluene and chloroform. The temperature for hydrolysis ranges from room temperature to 100° C. at which racemization will not occur. (It depends on the rate of hydrolysis of individual compounds.) The thus obtained optically active alcohols are recovered from the reaction liquid by solvent extraction (for separation from the optically active amino acids) and subsequent distillation.

Likewise, the optically active tartaric acid ester which has undergone diastereomer resolution is hydrolyzed so as to give the desired optically active alicyclic alcohol derivative. The hydrolysis of the ester group may be accomplished by either acid or alkali; but it should be carried out such that the desired alcohols do not undergo racemization. This object is achieved by reaction with an aqueous solution of mineral acid (such as sulfuric acid and hydrochloric acid) or an aqueous solution of alkali (such as sodium hydroxide, potassium hydroxide, sodium carbonate, and sodium hydrogen carbonate). Water as a medium may be used in combination with an organic solvent such as methanol, isopropanol, acetone, toluene, and chloroform. The temperature for hydrolysis ranges from room temperature to 100° C. at which racemization will not occur. (It depends on the rate of hydrolysis of individual compounds.) Hydrolysis by an alkaline aqueous solution involves the simultaneous hydrolysis of the acyl group of O,O'-diacyltartaric acid, giving rise to tartaric acid. Hydrolysis by an aqueous solution of mineral acid involves the slow hydrolysis of the acyl group of O,O'-diparatoluoyltartaric acid or O,O'-dibenzoyltartaric acid (under at certain condition of hydrolysis), giving rise to O,O'-diparatoluoyltartaric acid or O,O'-dibenzoyltartaric acid which can be recovered for reuse.

The thus obtained optically active alicyclic alcohol derivatives are recovered from the reaction liquid by solvent extraction (for separation from the optically active tartaric acid or derivatives thereof) and subsequent distillation.

The present invention permits the easy production of an optically active alcohol of high optical purity from a racemic alcohol, aid also permits the recycling of the recovered optically active amino acid or tartaric acid.

(6) Oxidation of alcohol

In the present invention, the oxidation of an alcohol to produce a ketone involves as reactants an alicyclic alcohol hypohalite, aliphatic compound, and mineral acid.

Preferred examples of the alicyclic alcohol include cycloalkanols (such as cyclopentanol, cyclohexanol, cycloheptanol, and cyclooctanol), alkyl-substituted cycloalkanol (such as 2-methylcyclohexanol and 3-methylcyclooctanol), and alkoxycycloalkanol (such as 2-methoxycyclohexanol). Preferred examples of the optically active alicyclic alcohol include optically active alkyl-substituted cycloalkanol (such as optically active 2-methylcyclohexanol and optically active 3-methylcyclooctanol) and optically active alkoxycycloalkanol (such as optically active 2-methoxycyclohexanol).

Preferred examples of the alkali metal or alkaline earth metal hypohalite include sodium hypochlorite, sodium hypobromite, potassium hypochlorite, potassium hypobromite, calcium hypochlorite, and calcium hypobromite. The former four are preferable and the first one is particularly preferable. Sodium hypochlorite may be used in the form of commercially available aqueous solution (5–14% concentrator). A dilute aqueous solution lower than 5% causes the reaction liquid to decrease in concentration, leading to an increased production cost. The aqueous solution of sodium hypochlorite may contain sodium chloride in any amount but should not contain free alkali (such as sodium hydroxide and potassium hydroxide) in an amount more than 1%. Excess free alkali should be neutralized beforehand; otherwise, it is necessary to adjust the amount of mineral acid to be added to the reaction liquid for oxidation.

The amount of alkali metal hypohalite to be used may be determined by the amount of effective chlorine. It is also affected by tie composition of the reaction system, the kind of the alicyclic alcohol, and the reaction temperature. Usually it s about 1–2 equivalents, preferably 1–1.3 equivalents, of the alicyclic alcohol. An amount less than 1 equivalent results in premature reactions, and an amount more than 2 equivalents leads to a high material cost and side reactions and the necessity of decomposing hypohalous acid after the reaction, An adequate amount of hypochlorous acid is 1–1.15 equivalents if the reaction proceeds satisfactorily.

The aliphatic compound is characterized by a partition ratio (defined below) greater than 1 and a solubility less than 5 wt % in water at 40° C. (To determine the partition ratio, a sample of alicyclic alcohol is dissolved in a sample of aliphatic compound and water (of the same amount as aliphatic compound). After stirring for 10 minutes, the, solution is allowed to stand at. 20° C. until the solution separates into two layers. The concentrations of alicyclic alcohol in the organic and aqueous layers are determined, and their ratio is calculated. A partition ratio greater than 1 means that the alicyclic alcohol is present more in the organic layer than in the aqueous layer.)

Preferred examples of the aliphatic compound include alkyl chloride (such as dichloromethane, chloroform, tetrachloromethane, monochloroethane, 1,1-dichloroethane, 1,2-dichloroethane, and 1,1,1- trichloroethane) and ethers (such as diethyl ether). Those except for the third and last ones are particularly desirable. (Their selection depends on the kind of alicyclic alcohol used). The amount of the aliphatic compound varies depending on the kind of alicyclic alcohol used; it is usually 0.1–3, preferably 0.2–1, times as much as alicyclic alcohol (by weight), An amount less than the minimum specified above is not enough to produce the desired effect at an adequate reaction rate without by-products. An amount more than the maximum specified above retards the reaction rate.

Preferred examples of the mineral acid include sulfuric acid, hydrochloric acid, and phosphoric acid in the form of aqueous solution. The mineral acid is used in an amount of 0.1–2 equivalents, preferably 0.2–0.8 equivalents, of the alicyclic alcohol used. An amount less than 0.1 equivalent is not enough to keep the reaction liquid acid (below pH 3) in opposition to the action of the alkali metal hypohalite which increases pH. This leads to a slow reaction rate and an increase in by-products. An amount more than 2 equivalents promotes the decomposition of hypohalous acid, making it necessary to increase the amount of alkali metal hypochlorite required to achieve 100% conversion of the alicyclic alcohol. This leads to an increased production cost. In the case where alkali metal hypohalite (in the form of aqueous solution) contains a large amount of free alkali; it is necessary to add an acid in an amount corresponding to the amount of free alkali at the initial stage or intermediate stage of reaction. One mol of sulfuric acid for one mol of alicyclic alcohol equals 2 equivalents. One mol of hydrochloric acid for one mol of alicyclic alcohol equals 1 equivalent. One mol of phosphoric acid for one mol of alicyclic alcohol equals 3 equivalents. The concentration of the aqueous solution of mineral acid should be 2–25 wt % preferably 5–15 wt %. A dilute aqueous solution of mineral acid (lower than 2%) lowers the concentration of the reaction liquid, aggravating the productivity. A concentrated aqueous solution of mineral acid (higher than 25%) results in too small an amount of reaction liquid for smooth operation in the initial stage of reaction. This presents difficulties in controlling the reaction temperature and increases by-products.

The reaction may be carried out by charging the alicyclic alcohol, aliphatic compound, and mineral acid ( aqueous solution) all at once and then adding dropwise the aqueous solution of alkali metal or alkaline earth metal hypohalite with stirring. It is also possible to add gradually the alicyclic alcohol and mineral acid (in aqueous solution) during reaction in the case where the mineral acid (in aqueous solution) has a high concentration in the initial stage or the amount of the aliphatic compound is small.

The reaction temperature should be 0–30° C., preferably 15–25° C., to keep stable the hypohalous acid which is formed in the reaction liquid. A reaction temperature lower than 0° C. leads to a slow rate of oxidation. A reaction temperature higher than 30° C. leads to the decomposition of hypohalous acid. In the case where an optically active aliphatic alcohol is used, it is desirable to keep the reaction temperature below 30° C. so as to suppress racemization.

The alkali metal hypohalite added to the reaction system becomes hypohalous acid immediately upon contact with the mineral acid, and the hypohalous acid immediately reacts with the alicyclic alcohol upon contact with it. Therefore, the reaction time substantially equals the time required for the aqueous solution of alkali metal hypohalite to be added. The reaction is followed by aging for about 30 minutes.

After the reaction is complete, excess hypohalous acid is decompose by adding, sodium hydrogensulfite until the reaction solution does not change potassium iodide starch paper into purple any longer.

The thus obtained alicyclic ketone is isolated from the reaction mixture in the usual way, such as extraction with an organic solvent, followed by solvent removal and distillation for purification, or followed by column chromatography for isolation and purification. In the case where the ketone is an optically active one, it is desirable to carry cut the following procedure to prevent racemization.

If there remains excess hypohalous acid, add alkali metal hydrogensulfite or alkali metal sulfite until the reaction solution does not change potassium iodide starch paper into purple any longer. (Alkali metal hydrogensulfite includes sodium hydrogensulfite, potassium hydrogensulfite, and lithium hydrogensulfite. Alkali metal sulfite includes sodium sulfite, potassium sulfite, and lithium sulfite.) They may be used in the form of aqueous solution or powder. The amount to be added depends on the amount of hypohalous acid remaining in the reaction system, It can be judged by visually observing that potassium iodide starch paper does not change into purple any longer.

The reaction solution containing the thus obtained alicyclic ketone is adjusted to PH 7.1–10, preferably PH 7.5–9, and then allowed to stand for 0.01–5 hours at 0–40° C. so as to decompose impurities unstable to bases. Preferred bases for PH adjustment include alkali metal hydroxide (such as sodium hydroxide, potassium hydroxide, and lithium hydroxide), alkali metal hydrogen carbonate (such as sodium hydrogen carbonate and potassium hydrogen carbonate), and alkali metal carbonate (such as sodium carbonate and potassium carbonate), Excessive alkalization (higher than pH 10) is not desirable because of the possibility of some optically active alicyclic ketones undergoing racemization.

The thus obtained reaction liquid undergoes extraction for separation of the desired optically active alicyclic ketone. Solvents for extraction are not specifically restricted so long as they are separable from water and capable of extracting the optically active alicyclic ketone without reacting with it. Examples of such solvents include ethers (such as dimethyl ether), ketones (such as methyl isobutyl ketone), hydrocarbons (such as cyclohexane and toluene), and alkyl halides (such as chloroform and dichloroethane.

After extraction, the extract containing the optically active alicyclic ketone is washed with a saturated aqueous solution of sodium chloride, (if necessary) dehydrated with magnesium sulfate or the like, concentrated, and distilled under reduced pressure.

According to the present invention, an alicyclic alcohol is oxidized with sodium hypochlorite in the presence of an aliphatic compound and a mineral acid. This procedure permits easy production of alicyclic ketone in high yields. The alicyclic ketone is characterized by immiscibility with water and a partition ratio in water greater than 1 (for the alicyclic alcohol as the starting material).

Using an optically active alicyclic alcohol as the starting material offers the advantage that it is possible to produce the desired optically active alicyclic ketone without racemization.

The alicyclic alcohol as the starting material and the alicyclic ketone as the reaction product usually have their respective melting points close to each other. Nevertheless, according to the present invention, it is possible to easily achieve 100% conversion for the alicyclic alcohol and hence it is possible to easily obtain the desired alicyclic ketone of high purity.

Moreover, according to the present invention, the optically active alicyclic alcohol is oxidized with a hypochlorite under an acidic condition, thereby converting it into an optically active alicyclic ketone, and distilling it under a basic condition, thereby giving an optically active alicyclic ketone of high purity with good storage stability.

(7) Storing Method

Since an optically active α-ketone is subject to racemization, it is desirable to store or stabilize it in the following manner.

(i) Storage in the absence of halogen.
(ii) Storage out of contact with oxygen.
(iii) Storage out of contact with metal.
(iv) Storage out of contact with acids and bases.
(v) Storage out of contact with inorganic oxides.
(vi) Storage in a condition created by combination of the above.

(i) Storage in the absence of halogen. This means that the environment for storage should not contain halogen in such an amount as to subject the optically active α-substituted cyclic ketone to racemization during its storage. In other words, the amount of halogen should be less than 500 ppm, preferably less than 200 ppm, of the optically active α-substituted cyclic ketone. The amount of halogen is determined by refluxing (with heating) a sample in 1N aqueous solution of sodium hydroxide and subsequently performing potentiometric titration.

Storing the optically active α-substituted cyclic ketone in the presence of a halogen-free solvent (after thorough stirring) produces good results. Examples of the halogen-free solvent include ketones (such as 2-butane), nitriles (such as acetonitrile), aliphatic hydrocarbons (such as hexane and octane), alicyclic hydrocarbons (such as cyclohexane), aromatic hydrocarbons (such as toluene), esters (such as ethyl acetate), ethers (such as diethyl ether and dioxane), and deoxygenated water). Of these examples, hydrocarbons and ethers are preferable. The concentration of the optically active α-substituted cyclic ketone in the solvent may range from 10 to 99 wt %. A solution with concentrations lower than 10 wt % is too bulky for efficient storage. A solution with concentrations higher than 99 wt % does not produce the effect of adding the solvent. The storage temperature varies depending on the quality of the distilled starting material and the optical and chemical purity required after storage. Storage at 20° C. will prevent the optical and chemical purity from decreasing by more than 3% even after storage for 60 days. Storage may be under pressure, normal pressure, or reduced pressure. A dark place or a container shielded from ultraviolet rays should preferably be used for storage.

(ii) Storage out of contact with oxygen. This is accomplished by blowing an oxygen-free inert gas into the purified product, thereby expelling oxygen completely, and then replacing the atmosphere in the container with an inert gas, or by expelling dissolved oxygen from the product in vacuo and then keeping the container evacuated or keeping the container filled with an inert gas (after introduction of an inert gas to break vacuum). The inert gas is any gas that does not react with the optically active α-substituted cyclic ketone. It is exemplified by nitrogen, helium, and argon. The inert gas atmosphere means any inert gas atmosphere in which the content of oxygen is less than 5%, preferably less than 1%. Storage may be under pressure, normal pressure, or reduced pressure. Storage at 20° C. will prevent the optical and chemical purity from decreasing by more than 1% even after storage for 60 days. A dark place or a container shielded from ultraviolet rays should preferably be used for storage. To ensure a better stability, it is recommended to mix the product with a halogen-free solvent (mentioned in (i) above) before storage in the atmosphere of inert gas.

(iii) Storage out of contact with metal. This is accomplished by storing the purified product in a glass container or a drum coated with halogen-free resin in place of a metal container or a stainless steel drum. In addition, it is not desirable to use a metal column and packing for rectification. Contact with metal promotes racemization and chemical degradation. Metals that have marked effects are iron, manganese, nickel, copper and zinc and alloys thereof.

(iv) Storage out of contact with acids and bases. This object is achieved when water has pH 3.5–7.5, preferably pH 4.5–7.5, that is in contact with the optically active α-substituted cyclic ketone. It is desirable to exclude inorganic acids (such as sulfuric acid and hydrochloric acid), inorganic bases (such as sodium hydrogen carbonate and sodium hydroxide), and organic bases (such as amines). The last one reacts with the carboxylic group in the optically active α-substituted cyclic ketone to lower the chemical purity.

The above-mentioned methods should preferably be used in combination with one another so as to keep stable the optically active α-substituted cyclic ketone which is unstable. That is, rectification should be carried out by using a glass-lined bubble cap tower or a glass-lined rectifying column containing plastic or glass packing (non-metal packing), and the distillate should be collected in glass containers or plastic-coated drums and stored under an inert gas atmosphere. Preferably, rectification should be carried out by using a glass-lined bubble cap tower or a glass-lined rectifying column containing plastic or glass packing (non-metal packing), the distillate should be diluted with a halogen-free solvent, and the resulting solution should be placed in glass containers or plastic-coated drums and stored under an inert gas atmosphere.

Storage may be under pressure, normal pressure, or reduced pressure. The storage temperature depends on the desired purity. Storage at 10° C. will prevent the optical and chemical purity from decreasing by more than 1% even after storage for 60 days.

Despite the above-mentioned procedure, racemization may take place if there are some kinds of impurities in trace amounts. In such a case, contact with an inorganic oxide prevents racemization and permits stable storage without chemical deterioration.

The optically active α-substituted ketone includes optically active aliphatic α-substituted ketones (such as optically active 3-methyl-2-oxoheptane), optically active alicyclic α-substituted ketones (such as optically active menthol and optically active 2-methoxycyclohexanol), and optically active aralkyl α-substituted ketones (such as optically active 2-methylpropylphenylketone). These compounds may be present in an organic solvent after extraction from the oxidation reaction solution, or in a concentrated solution remaining after solvent removal by distillation under reduced pressure from the organic extract layer, or in a vacuum distillate of said concentrated solution. Their concentration ranges from 1 to 99.9%. The inorganic oxide for contact includes, for example, zeolite and silica gel, which are capable of adsorbing polar substances. (Those which become a strong acid or a strong base in the system cannot be used.) Zeolite may be either natural zeolite or artificial zeolite, such as "Zeoram A-5" commercially available as molecular sieve from Toso Co., Ltd. An example of silica gel is "Wakogel C-200" from Wako Pure Chemical Industries, Ltd. These inorganic ozides may be used as such or after pretreatment for better effects. Pretreatment may be accomplished by heating at 100° C. for above (for drying) under reduced pressure, or by firing at 400° C. or above in an electric furnace.

The inorganic oxide may be brought into contact with the optically active α-substituted ketone by simply adding batchwise the former to the latter or by passing the latter through a column filled with the former. Either method may be used depending on the object. In the case of batchwise addition, the amount of the inorganic oxide should be 0.1–30 wt %, preferably 1–10 wt %, of the amount of the optically active α-substituted ketone, depending on the mode of storage, the amount of impurities, and the storage temperature. After the inorganic oxide has been added to the optically active α-substituted ketone (which may be present in an organic solvent or may contain an organic solvent as mentioned above), it is necessary to stir thoroughly but is not necessary to continue stirring. After stirring, the inorganic oxide (which has adsorbed impurities to promote racemization) may be filtered out or left in the system. After contact with the inorganic oxide, the optically active α-substituted ketone should be at 30° C. or below, preferably 10° C. or below, depending on the kind of the product and the desired optical and chemical purity of the product. In the case where the optically active α-substituted ketone is present in an extract of an organic solvent (which is not yet purified by distillation under reduced pressure) or in a concentrated solution remaining after solvent removal (by vacuum distillation) from the organic layer of the extract, the storage temperature should be lower than 0° C., preferably lower than −10° C. After contact with the inorganic oxide, the optically active α-substituted ketone should preferably be stored in vacuo or under an atmosphere of inert gas, such as nitrogen, helium, and argon, so as to avoid contact with oxygen.

According to the present invention, it is possible to keep chemically and optically stable the optically active α-substituted ketone which is chemically and optically unstable.

The optically active alcohol and optically active ketone obtained as mentioned above are useful as intermediates for organic reactions, particularly for preparing medicines and agricultural chemicals.

EXAMPLES

The invention will be described in more detail with reference to the following examples and comparative examples, which are not intended to restrict the scope of the invention.

(Production of Amino Acid Ester)

In this example, the analysis for optical purity by HPLC is carried out under the following basic conditions, although the eluent may vary in composition depending on individual compounds.

Column: Intersil ODS (made by G. L. Science)

Eluent: a mixture of 0.5% aq. solutions of phosphoric acid and acetonitrile in a ratio of from 20:80 to 80:20.

Flow rate: 2 ml/min

EXAMPLE 1

Figure 2:
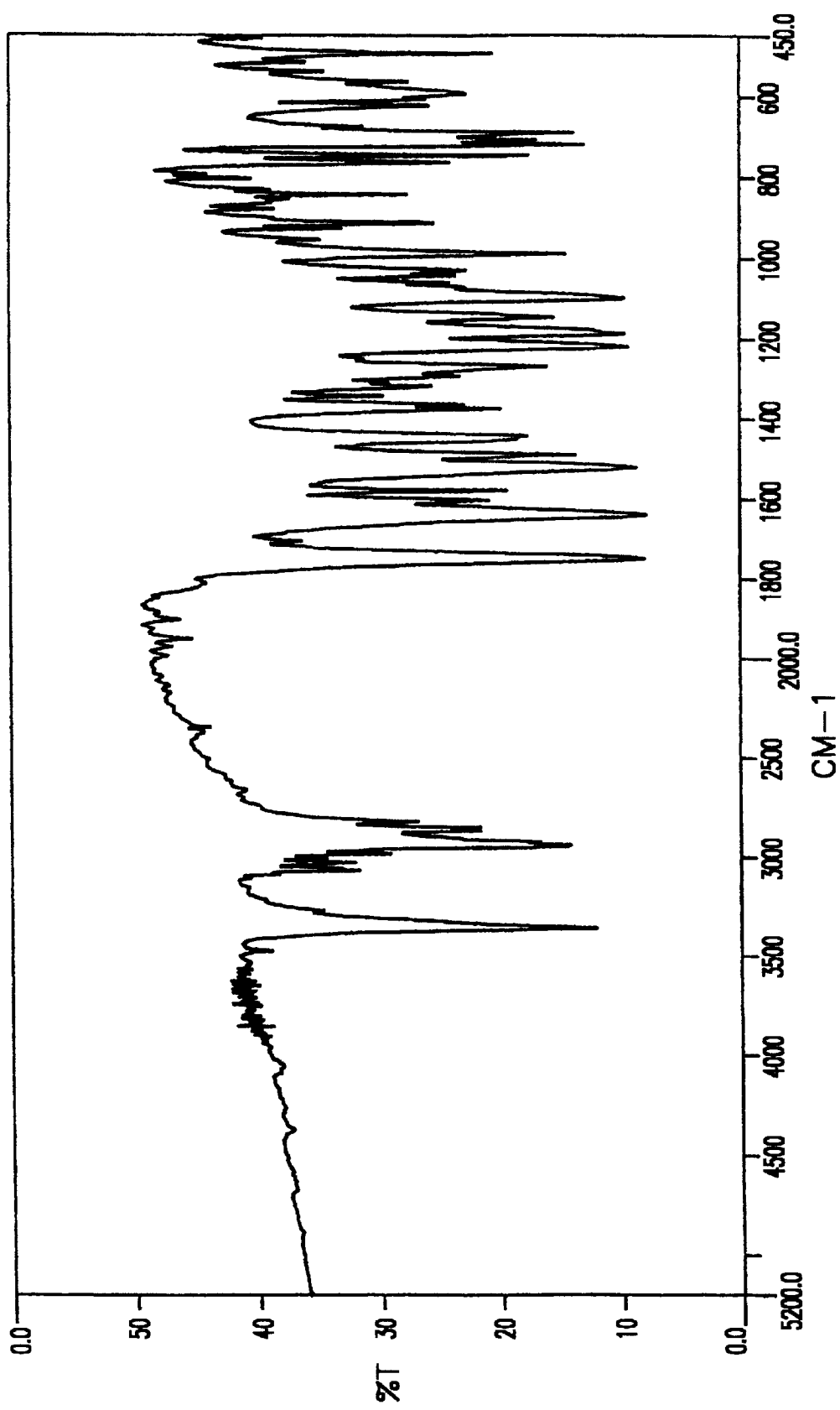
FIG. 2 is an IR chart of (1S)-(N-benzoyl-L-phenylalanyloxy)-(2S)-methoxycyclohexane obtained in Example 1.

A 500-ml four-mouth flask equipped with a thermometer, dropping funnel, condenser, and stirrer was charged with 27 g (0.1 mol) of N-benzoyl-L-phenylalanine and 300 ml of toluene. The flask was further charged with 13 g of thionyl chloride by dropwise addition over 30 minutes with stirring at 80–85° C. Stirring was continued for 1 hour. After the reaction was complete, the reaction solution was concentrated under reduced pressure and unreacted thionyl chloride and hydrochloric acid were removed. To the concentrated solution were added 14.3 g (0.11 mol) of trans-2-methoxycyclohexanol and 100 ml of toluene. After reaction at 80–90° C. for 2 hours, the reaction solution was concentrated under reduced pressure to give a mixture of (1S)-(N-benzoyl-L-phenylalaninyloxy)-(2S)-methoxycyclohexane and (1R)-(N-benzoyl-L-phenylalanyloxy)-(2R)-methoxycyclohexane. The concentrated solution was dissolved (with heating) in 150 ml of methanol added thereto, and the solution was cooled to room temperature and precipitates were filtered out. After drying, there was obtained 15.2 g of crystals. The crystals were found to be composed of (1S)-(N-benzoyl-L-phenylalanyloxy)-(2S)-methoxycyclohexane and (1R)-(N-benzoyl-L-phenylalanyloxy)-(2R)-methoxycyclohexane in a molar ratio of 4.6/1. The crystals were recrystallized from 200 ml of methanol to give 11.2 g of crystals composed of (1S)-(N-benzoyl-L-phenylalanyloxy)-(2S)-methoxycyclohexane and (1R)-(N-benzoyl-L-phenylalanyloxy)-(2R)-methoxycyclohexane in a molar ratio of 100/1. The (1S)-(N-benzoyl-L-phenylalanyloxy)-(2S)-methoxycyclohexane gave an NMR chart and an IR chart as shown in FIGS. 1 and 2, respectively. The NMR analysis was carried out by using JMMN-EX90 made by Nippon Denshi, with the same dissolved in CDCl3. The IR analysis was carried out by using SYSTEM 2000 made by Perkin-Elmer (KBr tablet method).

The crystals were dissolved in a mixture of 44 ml of 1N aqueous solution of sodium hydroxide and 20 ml of methanol, and the solution was kept at 40° C. for 2 hours to effect hydrolysis. The reaction solution was concentrated under reduced pressure to remove most ethanol. The concentrated solution was extracted three times with 20 ml of chloroform, and the extract was concentrated to give 3.7 g of (1S)-hydroxy-(2S)-methoxycyclohexane, which has an optical purity of 98% ee.

The aqueous layer remaining after extraction was made acidic and filtered out to recover crystals of N-benzoyl-L-phenylalanine. After drying, the recovered N-benzoyl-L-phenylalanine was reused to give the same results of resolution as mentioned above.

(Resolution of Amino Acid Ester)

EXAMPLE 2

Reaction was carried out between 27 g (0.1 mol) of N-benzoyl-L-phenylalanine and 13 g of thionyl chloride in the same manner as in Example 1. The reaction solution was concentrated under reduced pressure. The concentrated solution was given 13.4 g (0.11 mol) of α-phenylethyl alcohol and 100 ml of toluene, and reaction was carried out at 80–90° C. for 2 hours. After the reaction was complete, the reaction solution was concentrated and then given 50 ml of isopropanol. Resulting crystals were filtered off and recrystallized twice from 100 ml of isopropanol. The thus obtained crystals were hydrolyzed (in the same manner as in Example 1) and the resulting hydrolyzate was extracted with chloroform to give 5.2 g of α-phenylethyl alcohol. The optical purity of the S-form was 97% ee.

EXAMPLE 3

The same apparatus as used in Example 1 was charged with 23.8 g (0.1 mol) of N-paranitrobenzoyl-L-alanine, 14.3 g (0.11 mol) of trans-2-methoxycyclohexanol, and 200 ml of toluene. After stirring at 80–85° C., 13 g of thionyl chloride was added dropwise over 1 hour. Stirring was continued for 1 hour. The reaction solution was concentrated under reduced pressure. The residues were given 100 ml of isopropanol, followed by stirring at room temperature for 1 hour. Crystals that had separated out was filtered off. On hydrolysis with 2N aqueous solution of sodium hydroxide, there was obtained 5.2 g of trans-2-methoxycyclohexanol. The optical purity of the (R,R)-form was 58% ee.

EXAMPLE 4

Figure 3:
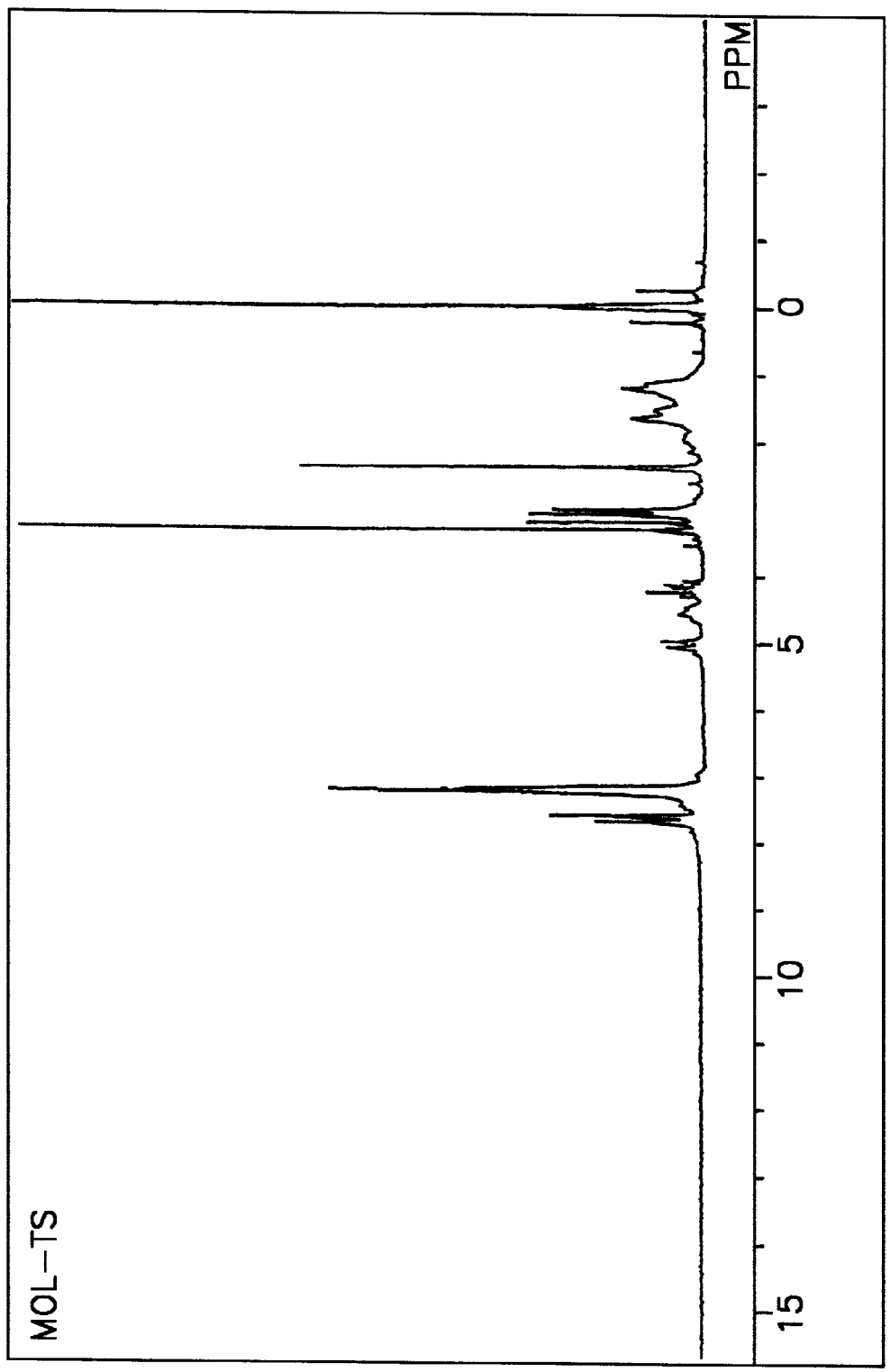
FIG. 3 is an NMR chart of (1S)-(N-tosyl-L-phenylalanyloxy)-(2S)-methoxycyclohexane obtained in Example 4.
Figure 4:
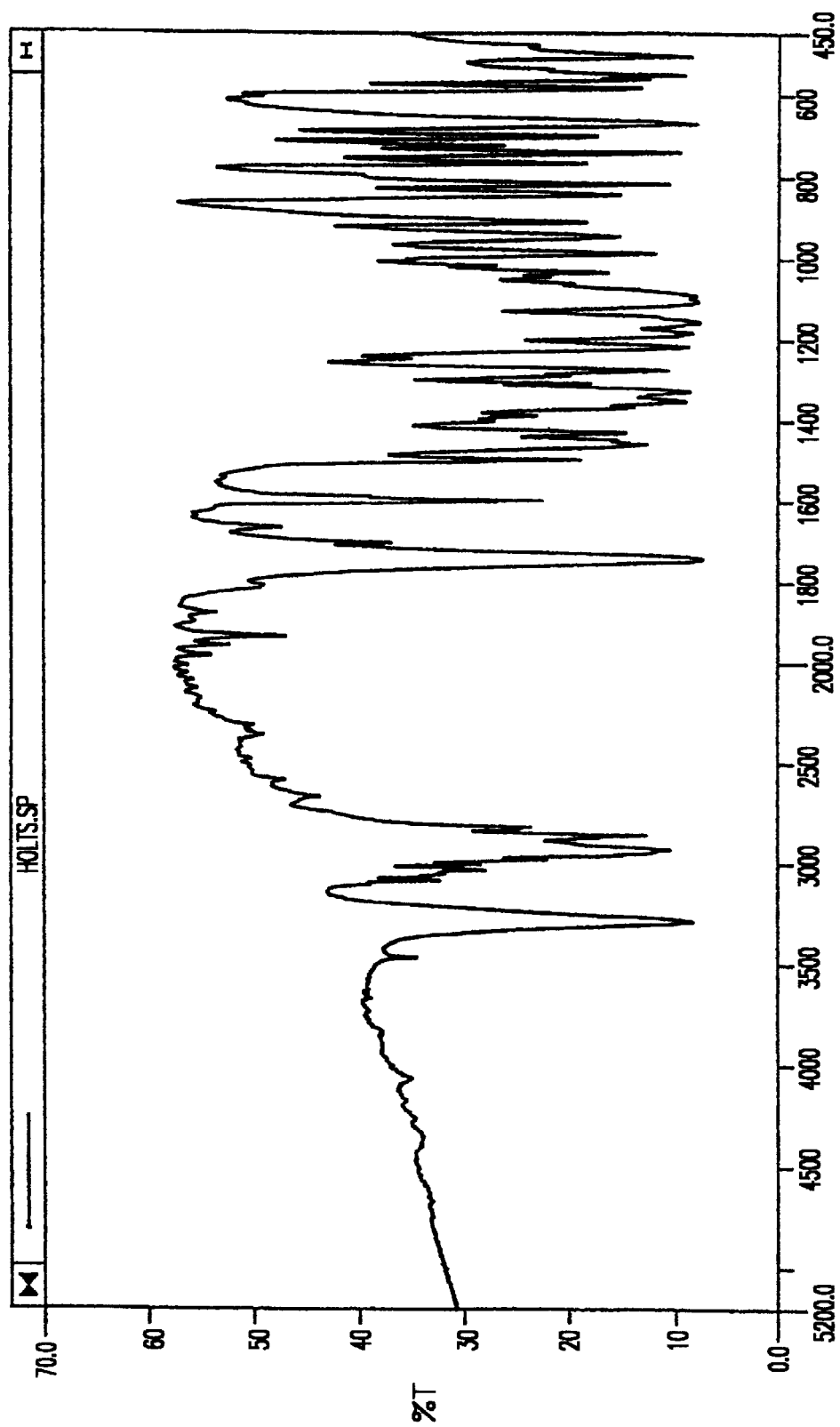
FIG. 4 is an IR chart of (1S)-(N-tosyl-L-phenylalanyloxy)-(2S)-methoxycyclohexane obtained in Example. 4.

The same apparatus as used in Example 1 was charged with 31.2 g (0.1 mol) of N-tosyl-L-phenylalanine, 14.3 g (0.11 mol) of trans-2-methoxycyclohexanol, 200 ml of toluene, and 1 g of paratoluenesulfonic acid. The reactants were heated under reflux for 5 hours. The reaction solution was concentrated and the residues were recyrstallized twice from 50 ml of isopropanol. Thus there was obtained 12.5 g of (1S)-(N-tosyl-L-phenylalanyloxy)-(2S)-methoxycyclohexane, which has an optical purity of 99% ee. This sample gave an NMR chart and an IR chart as shown in FIGS. 3 and 4, respectively. (Conditions for NMR and IR analyses are the same as those in Example 1.)

EXAMPLE 5

The procedure of Example 1 was repeated for reaction between 27 g (0.1 mol) of N-benzoyl-L-phenylalanine and 13 g of thionyl chloride. The reaction solution was concentrated under reduced pressure. The concentrated solution was reacted with 13.4 g (0.11 mol) of α-phenylethylalcohol and 100 ml of toluene at 80–90° C. for 2 hours. After the reaction was complete, the reaction solution was concentrated and the concentrated solution underwent chromatographic separation by the aid of a column (filled with 100 ml of silica gel) and a developing solvent consisting of cyclohexane and ethyl acetate in a ratio of 93:7 by volume. The fraction that had been eluted first was concentrated and then hydrolyzed to give 4.2 g of α-phenylethylalcohol. The optical purity of the S-form was 92% ee.

(Production of Tartaric Acid Ester)

In this example, the analysis for optical purity by HPLC was carried out under the following basic conditions, although the elutent may vary in composition depending on individual compounds.

Column: CAPSELL PAK SG 120, 4.6 mm in diameter, 150 mm long (made by Shiseido Co., Ltd.)

Eluent: a mixture of 0.05% aq. solutions of phosphoric acid and acetonitrile in a ratio of 55:45.

Flow rate: 1 ml/min

Detector: UV 254 nm

EXAMPLE 6

Figure 5:
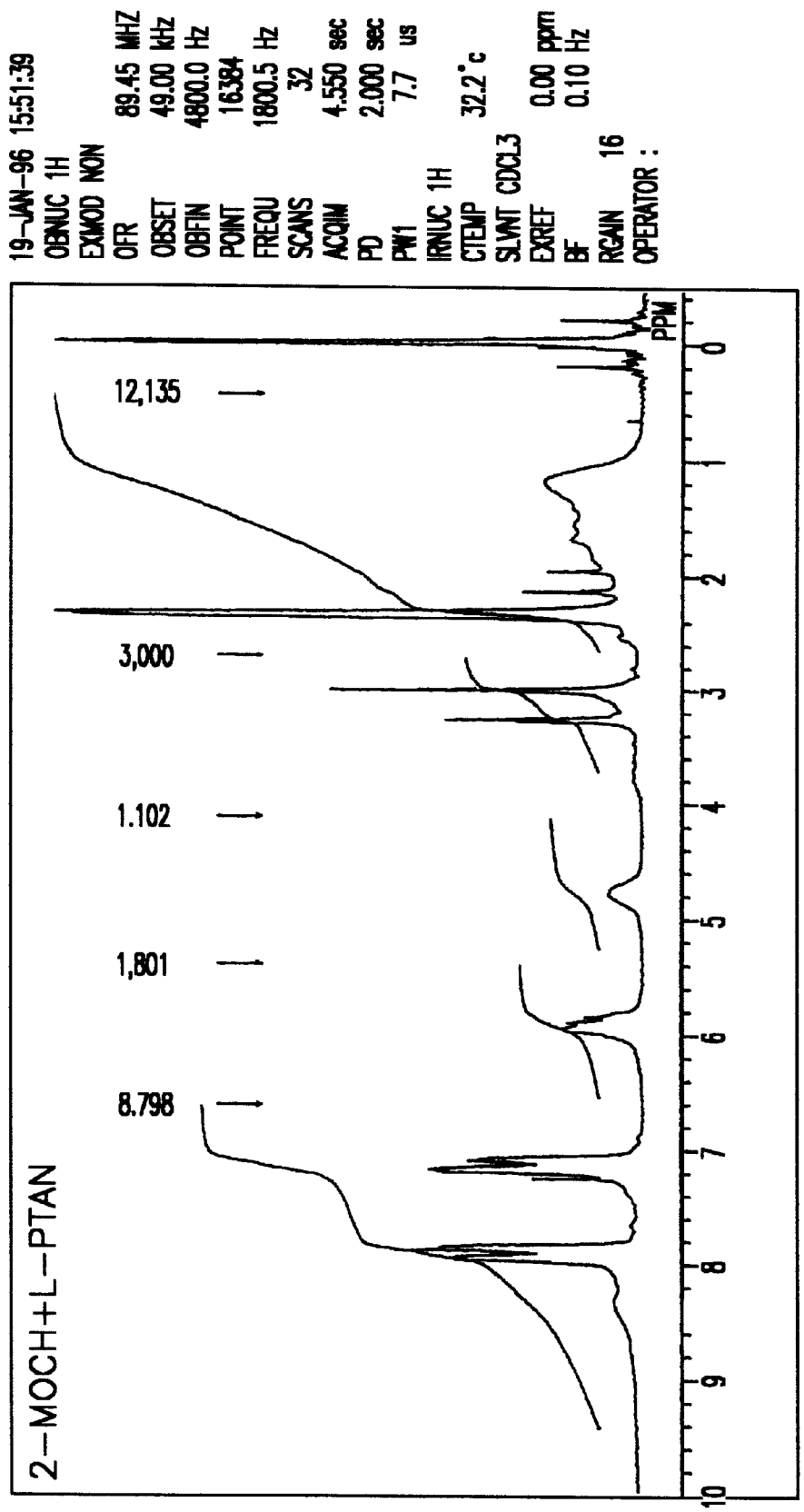
FIG. 5 is an 1H-NMR chart of the compound obtained in Example 6.
Figure 6:
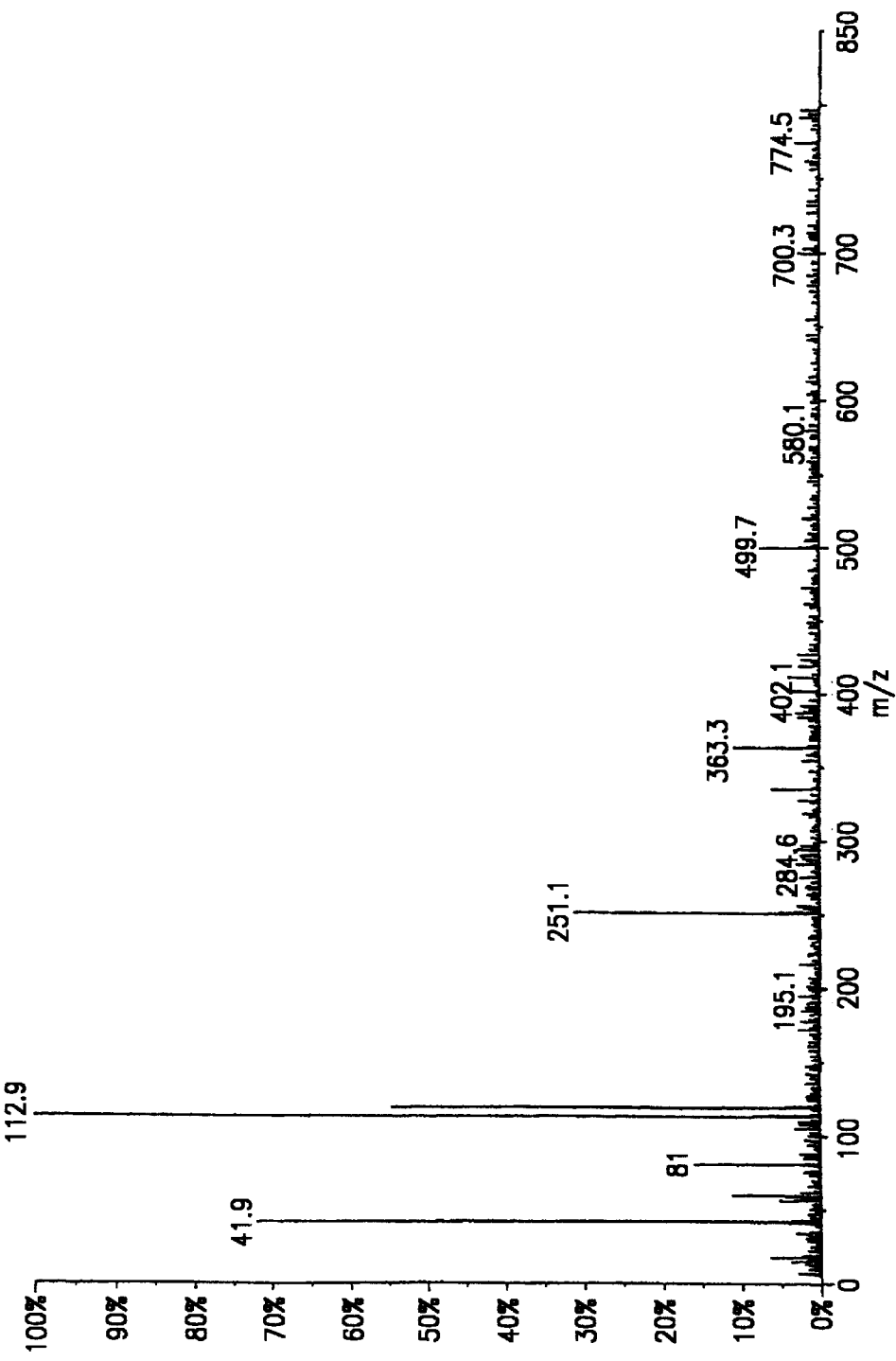
FIG. 6 is an MS spectrum of the compound obtained in Example 6.

A 500-ml four-mouth flask equipped with a thermometer, dropping funnel, condenser, and stirrer was charged with 47.8 g (0.13 mol) of diparatoluoyl-L-tartaric acid anhydride, 13.0 g (0.1 mol) of (RS)-2-methoxycyclohexanol, 1.2 g of anhydrous iron trichloride, and 300 ml of toluene. After heating under reflux for 10 hours, the reaction solution was analyzed by liquid chromatography. The result of analysis indicated the formation of diparatoluoyl-L-tartaric acid-mono(2-methoxy)cyclohexyl ester (92%).Time for peak detection was 35 minutes in the case of (R)-2-methoxycyclohexanol ester and 37 minutes in the case of (S)-2-methoxycyclohexanol ester. These analytical data suggest that the tartaric acid ester formed is composed of (R)-form and (S)-form in a ratio of approximately 1/1. The reaction solution was filtered to separate the diparatoluoyl-L-tartaric acid anhydride remaining unreacted. The filtrate was concentrated and subjected to column chromatography (using a column filled with silica gel "Kieselgel 60", 60–230 mesh, made of Merck). Chromatographic separation was carried out by using a mixture of acetonitrile and cyclohexane in varied ratios. Thus there was obtained 9.5 g of diparatoluoyl-L-tartaric acid-mono(R)-2-methoxycyclohexyl ester. Analysis by liquid chromatography indicated that the optical purity of the (R)-ester if 98% ee. This compound gave an 1H-NMR chart (CDCl₃) and an MS spectrum as shown in FIGS. 5 and 6, respectively.

EXAMPLE 7

Figure 7:
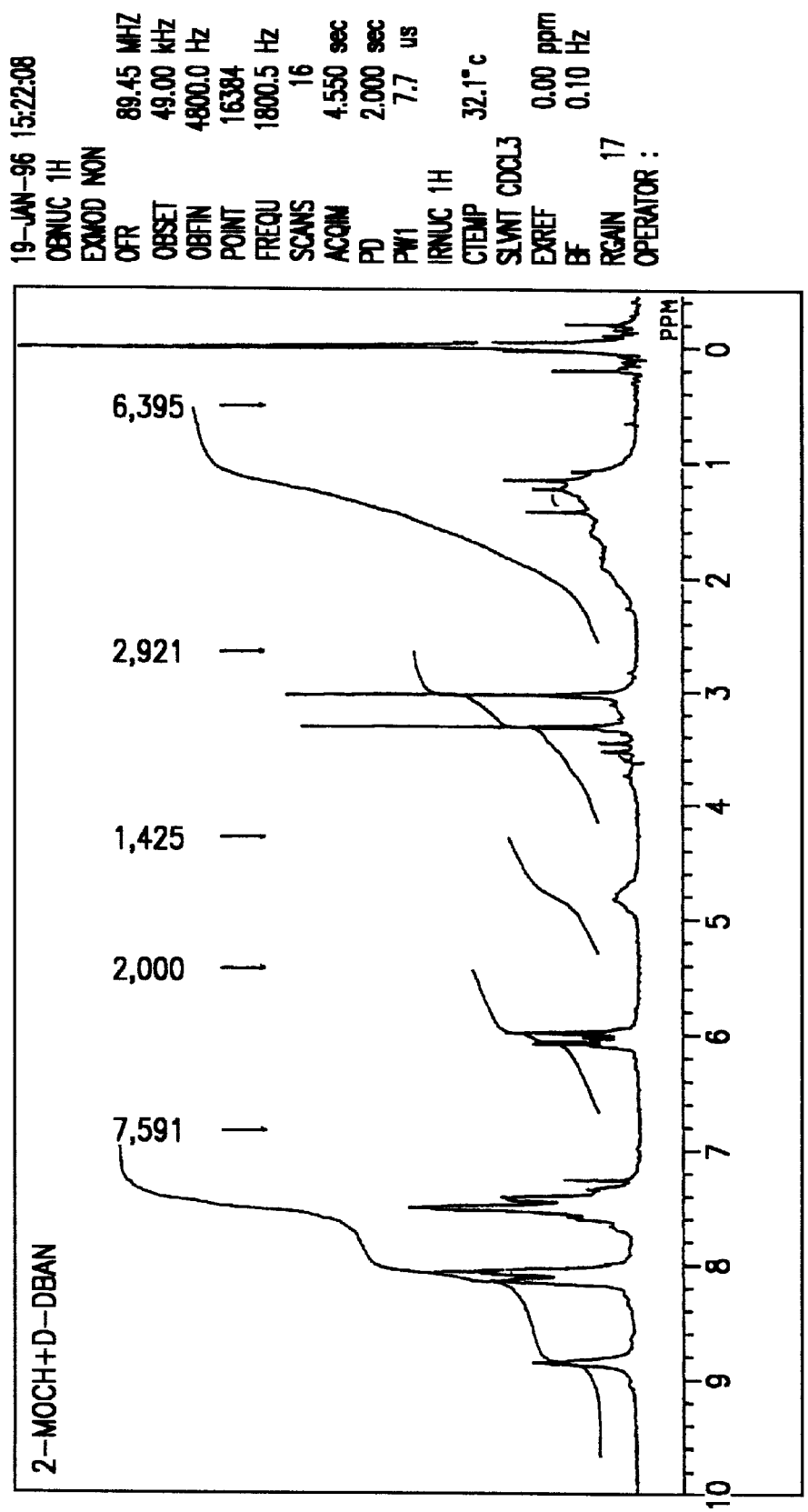
FIG. 7 is an 1H-NMR chart of the compound obtained in Example 7.

A 500-ml four-mouth flask equipped with a thermometer, dropping funnel, condenser, and stirrer was charged with 51.0 g (0.15 mol) of dibenzoyl-L-tartaric acid anhydride, 13.0 g (0.1 mol) of (RS)-2-methoxycyclohexanol, 1.2 g of anhydrous iron trichloride, and 300 ml of toluene. After heating under reflux for 10 hours, the reaction solution was analyzed by liquid chromatography. The result of analysis indicated the formation of dibenzoyl-L-tartaric acid-mono (2-methoxy)cyclo- hexyl ester (95)%. Time for peak detection was 17 minutes in the case of (R)-2-methoxycyclohexanol ester and 18 minutes in the case of (S)-2-methoxycyclohexanol ester. These analytical data suggest that the tartaric acid ester formed is composed of (R)-form and (S)-form in a ratio of approximately 1/1. The reaction solution was filtered to separate insoluble matter. The filtrate was concentrated and subjected to column chromatography (using a column filled with silica gel "Kieselgel 60", 60–230 mesh, made by Merck). Chromatographic separation was carried out by using a mixture of acetonitrile and cyclohexane in varied ratios. Thus there was obtained 10.8 g of dibenzoyl-L-tartaric acid-mono(R)-2-methoxycyclohexyl ester. Analysis by liquid chromatography indicated that the optical purity of the (R)-ester is 96% ee. This compound gave an 1H-NMR chart (CDCl₃) as shown in FIG. 7.

EXAMPLE 8

The same apparatus as used in Example 6 was charged with 2.5 g (0.02 mol) of α-phenylethylalcohol, 14.7 g (0.04 mol) of diparatoluoyl-L-tartaric acid anhydride, 37 mg of anhydrous iron trichloride, and 60 g of toluene. After heating under reflux for 5 hours, the reaction solution was analyzed by liquid chromatography. The result of analysis indicated the formation of diparatoluoyl-L-tartaric acid-mono(RS)-α-phenylethyl ester (88%). Time for peak detection was 37 minutes in the case of (R)-α-phenylethylalcohol ester and 43 minutes in the case of (S)-α-phenylethylalcohol ester. These analytical data suggest that the tartaric acid ester formed is composed of (R)-form and (S)-form in a ratio of approximately 1.2/1. The reaction solution was filtered to separate insoluble matter. The filtrate was concentrated and subjected to column chromatography (using a column filled with silica gel "Kieselgel 60", 60–230 mesh, made by Merck). chromatographic separation was carried out by using a mixture of acetonitrile and cyclohexane in varied ratios. Thus there was obtained 3.1 g of diparatoluoyl-L-tartaric acid-mono (R)-α-phenylethylalcohol ester. Analysis by liquid chromatography indicated that the optical purity of the (R)-ester is 96% ee.

EXAMPLE 9

A 500-ml four-mouth flask equipped with a thermometer, dropping funnel, condenser, and stirrer was charged with 47.8 g (0.13 mol) of diparatoluoyl-L-tartaric acid anhydride, 13.0 g (0.1 mol) of (RS)-2-methoxycyclohexanol, 1.2 g of anhydrous iron trichloride, and 300 ml of toluene. After heating under reflux for 10 hours, the reaction solution was analyzed by liquid chromatography. The result of analysis indicated the formation of diparatoluoyl-L-tartaric acid-mono(2-methoxy)cyclohexyl ester (92%). Time for peak detection was 35 minutes in the case of (R)-2-methoxycyclohexanol ester and 37 minutes in the case of (S)-2-methoxycyclohexanol ester. Diparatoluoyl-L-tartaric acid anhydride remaining unreacted was filtered off, and the filtrate was concentrated and subjected to column chromatography (using a column filled with silica gel "Kieselgel 60", 60–230 mesh, made by Merck). Chromatographic separation was carried out by using a mixture of acetonitrile and cylohexane in varied ratios. There was obtained 9.5 g of diparatoluoyl-L-tartaric acid-mono(R)-2-methoxycyclohexyl ester in the first eluate. Analysis by liquid chromatography indicated that the ester is composed of (R)-form and (S)-form in a ratio of approximately 99/1. This compound was hydrolyzed by 30 ml in 1N aqueous solution of sodium hydroxide at 30° C. for 5 hours with stirring. The hydrolyzate was extracted three times with 100 ml of dichloroethane. The extract was concentrated to give 2.8 g of concentrated solution containing (R)-2-methoxycyclohexanol. The concentrated solution was distilled under reduced pressure (2.6 kPa) to give 2.2 g of distillate having an angle of rotation of −75° (c=2.10 in dichloromethane). The last eluate obtained by chromatographic separation was treated in the same manner as above to give 2.1 g of (S)-2-methoxycyclohexanol having an angle of rotation of +74° (c=2.00 in dichloromethane).

EXAMPLE 10

The procedure of Example 7 was repeated to give a concentrated solution containing about 20 g of dibenzoyl-L-tartaric acid-mono(R)-2-methoxycyclohexyl ester. This concentrated solution was subjected to column chromatography (using a column filled with silica gel "Kieselgel 60", 60–230 mesh, made by Merck). chromatographic separation was carried out by using a mixture of acetonitrile and cyclohexane in varied ratios. The eluate was concentrated to give 5.8 g of dibenzoyl-L-tartaric acid-mono(R)-2-methoxycyclohexyl ester. The liquid chromatography under the above-mentioned conditions caused (R)-2-methoxycyclohexanol ester to be detected after 17 minutes and (S)-2-methoxycyclohexanol ester to be detected after 18 minutes. Results of analysis indicated that the concentrated solution consisted of (R)-ester and (S)-ester in a ratio of 98/2. Upon treatment in the same manner as in Example 9, followed by distillation under reduced pressure, there was obtained (R)-2-methoxycyclohexanol.
(Oxidation)

Example 11

A 500-ml four-mouth flask equipped with a thermometer, dropping funnel, condenser, and stirrer was charged with 13.0 g (0.1 mol) of (RS)-2-methoxycyclohexanol, 7 g of dichloromethane, and 30 g of 10% aqueous solution of sulfuric acid (30 mmol). The reactants were stirred at 20–25° C. The flask was further charged with 60 g of aqueous solution of sodium hypochlorite containing 12.1% effective chlorine over about 1 hour. Stirring was continued for 30 minutes. The reaction solution was analyzed by gas chromatography to confirm that the peak due to (RS)-2-methoxycyclohexanol had disappeared. The reaction solution was given 2 g of sodium hydrogensulfite with stirring. It was confirmed that the reaction solution did not change potassium iodide starch paper into purple any longer. The reaction solution was extracted twice with 50 g of dichloromethane. The dichloromethane layers were combined together and washed with 30 g of saturated aqueous solution of sodium chloride. Upon concentration and distillation, there was obtained 11.5 g (90 mmol) of (RS)-2-methoxycyclohexanone. The chemical purity of this compound was 99.8%. Incidentally, the dichloromethane used in this example has a partition ratio in water (at 20° C.) greater than 1 and has a solubility in water (40° C.) lower than 5 wt %.

Example 12

The same apparatus as used in Example 1 was charged with 11.4 g (0.1 mol) of (RS)-2-methylcyclohexanol, 7 g of 1,2-dichloroethane, and 20 g of 10% aqueous solution of sulfuric acid (20 mmol). The reactants were stirred at 20–25° C. The flask was further charged with 145 g of aqueous solution of sodium hypochlorite containing 5.6% effective chlorine over about 3 hours. Stirring was continued for 30 minutes. The result of analysis by gas chromatography indicated the formation of (RS)-2-methylcyclohexanone (95%). Incidentally, the 1,2-dichloroethane used in this example has a partition ratio in water (at 20' C.) greater than 1 and has a solubility in water (40° C.) lower than 5 wt %.

Example 13

The same apparatus as used in Example 1 was charged with 11.4 g (0.1 mol) of (RS)-4-methylcyclohexanol, 10 g of chloroform, and 20 g of 10% aqueous solution of sulfuric acid (20 mmol). The reactants were stirred at 20–25° C. The flask was further charged with 145 g of aqueous solution of sodium hypochlorite containing 5.6% effective chlorine over about 3 hours. Stirring was continued for 30 minutes. The result of analysis by gas chromatography indicated the formation of (RS)-4-methylcyclohexanone (94%). Incidentally, the chloroform used in this example has a partition ratio in water (at 20° C.) greater than 1 and has a solubility in water (40° C.) lower than 5 wt %.

Example 14

The same procedure as in Example 1 was repeated to give 11.2 g (88 mmol) of (S)-2-methoxycyclohexanone from 13.0 g (0.1 mol) of (S)-2-methoxycyclohexanol having an optical purity of 99% ee. This product has a chemical purity of 99.8% and an optical purity of 99% ee. Racemization did not occur during reaction.

Example 15

The same apparatus as used in Example 11 was charged with 3.9 g (30 mmol) of (RS)-4-methylcyclohexanol, 7 g of 10% hydrochloric acid (19 mmol), and 2 g of diethyl ether. By dropping 23 g of 12.3% aqueous solution of hypochlorite, reaction was carried out in the same manner as in Example 1. The result of analysis by gas chromatography indicated the formation of (RS)-2-methylcyclohexanone (95%). Incidentally, the diethyl ether used in this example has a partition ratio in water (at 20° C.) greater than 1 and has a solubility in water (40° C.) lower than 5 wt %.

Comparative Example 1

The same procedure as in Example 11 was repeated except that 10% sulfuric acid was not added. The result of analysis by gas chromatography indicated the formation of (RS)-2-methoxycyclohexanol (1.7%).

Comparative Examples 2 to 6

The same apparatus as used in Example 11 was charged with 11.4 g (0.1 mol) of (RS)-2-methoxycyclohexanol, the compound shown in Table 1, and 40 g of 10% aqueous solution of sulfuric acid (41 mmol). The reactants were stirred at 20–25° C. The reaction solution was given 65 g of aqueous solution of sodium hypochlorite containing 12.5% effective chlorine over about 2 hours. Stirring was continued for 30 minutes. The results are shown in Table 1. Incidentally, the methanol and acetonitrile used in these comparative examples had a solubility in water (40° C.) higher than 5 wt %. The partition (at 20° C.) of (RS)-2-methoxycyclohexanol is much greater in water than in cyclohexane, and the partition ratio for cyclohexane is lower than 1.

TABLE 1

|  | Compound | Amount added | Conversion (%) | Yield of (RS)-2-methoxycyclohexanone (%) |
|---|---|---|---|---|
| Comparative Example 2 | None |  | 41.9 | 38.7 |
| Comparative | Methanol | 100 g | 76.5 | 69.3 |

TABLE 1-continued

| Compound | | Amount added | Conversion (%) | Yield of (RS)-2-methoxycyclohexanone (%) |
|---|---|---|---|---|
| Example 3 | | | | |
| Comparative Example 4 | Methanol | 13 g | 76.2 | 69.3 |
| Comparative Example 5 | Acetonitrile | 13 g | 85.4 | 79.8 |
| Comparative Example 6 | Cyclohexane | 30 g | 10.2 | 8.6 |

It is noted that in these comparative examples the conversion of (RS)-2-methoxycyclohexanol is low and the selectivity of (RS)-2-methoxycyclohexanone is low.

Comparative Example 7

The same apparatus as used in Example 11 was charged with 11.4 g (0.1 mol) of (RS)-2-methoxycyclohexanol, 7 g of methyl ethyl ketone, and 25 g of 10% aqueous solution of sulfuric acid (26 mmol). The reactants were stirred at 20–25° C. The reaction solution was given 61 g of aqueous solution of sodium hypochlorite containing 12.5% effective chlorine over about 2 hours. Stirring was continued for 30 minutes. The result of analysis by gas chromatography indicated the formation of (RS)-2-methocycyclohexanone (93%), with the conversion of (RS)-2-methoxycyclohexanol being 98%.

Then, the same procedure as in Example 1 was repeated to extract (RS)-2-methoxycyclohexanol with chloroform. During extraction, the methyl ethyl ketone was chlorinated to give a compound having strong tearing properties, which hindered the subsequent operation. Incidentally, the methyl ethyl ketone used in this comparative example has a solubility in water (40° C.) lower than 5 wt %.

Comparative Example 8

The same procedure as in Comparative Example 6 was repeated except that methyl ethyl ketone was replaced by toluene. The result of analysis by gas chromatography indicated that the conversion of (RS)-2-methocycyclohexanone was 45% and the yield of (RS)-2-methocycyclohexanol was as low as 42%. In addition, the reaction gave rise to chlorinated toluene as a by-producy, which made it necessary to use a rectifying column having a large number of plates to purify (RS)-2-methocycyclohexanol. The partition (at 20° C.) of (RS)-2-methoxycyclohexanol is much greater in water than in toluene, and the partition ratio for toluene is lower than 1.

Comparative Example 9

The same procedure as in Example 11 was repeated except that 40 g of 25% sulfuric acid was added. The result of analysis by gas chromatography indicated that 24% of (RS)-2-methoxycyclohexanol remained unreacted.
(Production of optically active ketone)

In the following examples, the chemical purity of optically active alicyclic ketone was determined by gas chromatography that employs "Thermon 3000" as the liquid layer, and the optical purity was determined by gas chromatography that employs a chiral column.

Example 16

A 500-ml four-mouth flask equipped with a thermometer, dropping funnel, condenser, and stirrer was charged with 13.0 g (0.1 mol) of (S)-2-methoxycyclohexanol having an optical purity of 99.8% ee, 7 g of dichloromethane, and 30 g of 10% aqueous solution of sulfuric acid (30 mmol). The reactants were stirred at 20–25° C. The flask was further charged with 60 g of aqueous solution of sodium hypochlorite containing 12.1% effective chlorine over about 1 hour. Stirring was continued for 30 minutes. The reaction solution was analyzed by gas chromatography to confirm that the peak due to (S)-2-methoxycyclohexanol had disappeared. The reaction solution was given 2 g of sodium hydrogensulfite with stirring. It was confirmed that the reaction solution did not change potassium iodide starch paper into purple any longer. The reaction solution was extracted twice with 200 g of dichloromethane. The dichloromethane layers were combined together and washed with 30 g of 30% aqueous solution of sodium carbonate. After stirring at 20–25° C. for 1 hour, it was confirmed that the water layer had a pH higher than 7.5. The water layer was discharged, and the dichloromethane layer was washed with saturated aqueous solution of sodium chloride. Upon concentration and distillation, there was obtained 11.5 g (90 mmol) of (S)-2-methoxycyclohexanone. The chemical purity of this compound was 99.6%. One gram of this compound was placed in a glass ample and sealed, with the atmosphere therein replaced with argon. The ample was heated at a prescribed temperature for 60 hours. After cooling to room temperature, the ample was opened and the content was tested for optical purity. The results are shown in Table 2.

TABLE 2

| Heating temperature | Optical purity |
|---|---|
| 60° C. | 99.6% ee |
| 80° C. | 98.9% ee |
| 100° C. | 97.3% ee |

Example 17

Reaction was carried out in the same manner as in Example 16. After the peak due to (S)-2-methoxycyclohexanol had disappeared, the reaction solution was given 2 g of sodium hydrogensulfite with stirring so that the reaction solution did not change potassium iodide starch paper into purple any longer. The reaction solution was adjusted to pH 2 or below with 10% sulfuric acid, followed by stirring at 20–25° C. for 1 hour. The reaction solution was adjusted to pH 7.5–8 with an aqueous solution of sodium carbonate, followed by stirring at 20–25° C. for 1 hour. The reaction solution was adjusted again to pH 2 or below with 10% sulfuric acid, followed by stirring at 20–25° C. for 2 hours. The reaction solution was extracted three times with 100 g of toluene. The toluene layers were combined together and washed with a saturated aqueous solution of sodium chloride. After concentration and distillation in the same manner as in Example 1, there was obtained 10.3 g (80 mmol) of (S)-2-methoxycyclohexanone having a chemical purity of 99.3% and an optical purity of 99.6% ee. This product was heated at 60° C. for 48 hours in the same manner as in Example 16; it decreased in optical purity to 99.0% ee.

Example 18

The same procedure as in Example 16 was repeated except that the dichloroethylene was replaced by ethyl hexyl ketone. There was obtained 9.9 g of (S)-2-methoxycyclohexanone having an optical purity of 99.2% ee. This product was heated at 60° C. for 48 hours in the same manner as in Example 16; it decreased in optical purity to 98.5% ee.

Comparative Example 10

Reaction was carried out in the same manner as in Example 16. After the peak due to (S)-2-methoxycyclohexanol had disappeared, the reaction solution was given 2 g of sodium hydrogensulfite with stirring so that the reaction solution did not change potassium iodide starch paper into purple any longer. The reaction solution was extracted twice with 100 g of dichloroethane. The dichloroethane layers were combined together and washed with a saturated aqueous solution of sodium chloride. After concentration and distillation in the same manner as in Example 1, there was obtained 10.9 g (85 mmol) of (S)-2-methoxycyclohexanone having a chemical purity of 99.4% and an optical purity of 99.5% ee (measured immediately after distillation). As in Example 3, this product was sealed in a glass ample, with the atmosphere therein replaced with argon. The glass ample was heated at a prescribed temperature for 20 hours. After cooling to room temperature, the ample was opened and the content was tested for optical purity. The results are shown in Table 3.

TABLE 3

| Heating temperature | Optical purity |
| --- | --- |
| 20° C. | 75.6% ee |
| 40° C. | 38.2% ee |
| 60° C. | 11.3% ee |

(Storage of optically active ketone)

In the following examples, the chemical purity of optically active 2-methoxycyclohexanone was determined by gas chromatography that employs "Thermon 3000" as the liquid layer, and the optical purity was determined by gas chromatography that employs a chiral column.

Example 19

A sample of (S)-2-methoxycyclohexanone (having an optical purity of 98.75% ee and a chemical purity of 99.28%) was distilled using a glass apparatus. The distillate (1 g) was diluted with a prescribed solvent to give a 50 wt % solution. The solution was sealed in a glass ample, with the atmosphere therein replaced with argon. The ample was heated at 80° C. for 65 hours. After cooling to room temperature, the ample was opened and the content was tested for optical purity and chemical purity. The results are shown in Table 4.

TABLE 4

| Solvent | Optical purity (% ee) | Chemical purity (%) |
| --- | --- | --- |
| None | 98.05 | 99.07 |
| 2-Butanone | 98.58 | 99.27 |
| Acetonitrile | 98.58 | 99.25 |
| Aliphatic hydrocarbon (bp. 100–120° C.) | 98.57 | 99.28 |
| Cyclohexane | 98.48 | 99.19 |
| Ethyl acetate | 98.39 | 99.15 |
| 1,4-Dioxane | 98.28 | 97.19 |
| Propylene glycol | 98.26 | 99.87 |
| Water (deoxygenated) | 98.14 | 99.07 |
| Toluene | 98.13 | 98.59 |

Example 20

A sample of (S)-2-methoxycyclohexanone (the same one as in Example 19) was diluted with cyclohexane to give a 50 wt % solution. The solution was sealed in a glass ample, with the atmosphere therein replaced with argon. The ample was stored at room temperature (20–25° C.) for one month. The ample was opened and the content was analyzed. The optical purity was 98.68% ee and the chemical purity was 99.27%.

Example 21

A sample of (S)-2-methoxycyclohexanone (the same one as in Example 19) was diluted with cyclohexane to give a 50 wt % solution. The solution was sealed in a glass ample. The ample was stored at 20° C. for 60 days. The ample was opened and the content was analyzed. The optical purity was 95.89% ee and the chemical purity was 96.18%.

Example 22

A sample of (S)-2-methoxycyclohexanone (the same one as in Example 19) was sealed in a glass ample, with the atmosphere therein replaced with nitrogen. The ample was stored at 20° C. for 60 days. The ample was opened and the content was analyzed. The optical purity was 98.05% ee and the chemical purity was 99.07%.

Example 23

A sample of (S)-2-methoxycyclohexanone (having an optical purity of 99.02% ee and a chemical purity of 99.13% ) was distilled using a glass apparatus. The distillate (1 g) was diluted with toluene to give a 90 wt % solution. The solution was sealed in a glass ample, with the atmosphere therein replaced with argon. The ample was stored at 10° C. for 6 months. The ample was opened and the content was analyzed. The optical purity was 98.08% ee and the chemical purity was 99.05%.

Example 24

A sample of (S)-2)-methoxycyclohexanone (the same one as in Example 19) was diluted with a prescribed solvent to give a 50 wt % solution. The solution was sealed in a glass ample, without the atmosphere therein replaced with inert gas. The ample was heated at 80° C. for 65 hours. The ample was opened and the content was tested for optical purity and chemical purity. The results are shown in Table 5.

TABLE 5

| Solvent | Optical purity (% ee) | Chemical purity (%) |
| --- | --- | --- |
| 2-Butanone | 98.21 | 96.92 |
| Cyclohexane | 98.03 | 96.87 |
| Ethyl acetate | 97.99 | 95.58 |
| Toluene | 97.38 | 97.93 |

Comparative Example 11

A sample of (S)-2-methoxycyclohexanone (the same one as in Example 19) as such (without dilution) was sealed in a glass ample, without the atmosphere therein replaced with inert gas. The ample was heated at 80° C. for 65 hours as in Example 19. The ample was opened and the content was analyzed. It was found that the optical purity decreased to 97.10% ee and the chemical purity decreased to 95.12%.

Comparative Example 12

A sample of (S)-2-methoxycyclohexanone (the same one as in Example 19) was diluted with a halogen-containing solvent to give a 50 wt % solution. The solution was sealed in a glass ample, with the atmosphere therein replaced with argon. The ample was heated at 80° C. for 65 hours. The ample was opened and the content was tested for optical purity and chemical purity. The results are shown in Table 6.

TABLE 6

| Solvent | Optical purity (% ee) | Chemical purity (%) |
|---|---|---|
| Chlorobenzene | 97.70 | 98.94 |
| 1,2-Dichloroethane | 9.70 | 96.64 |
| 1,1,1-trichloroethane | 0.00 | 94.50 |

Comparative Example 13

A sample of (S)-2-methoxycyclohexanone (the same one as in Example 19) as such (without dilution) was heated together with a piece of stainless steel at 80° C. for 65 hours in the same manner as in Example 19. The ample was opened and the content was analyzed. It was found that the optical purity decreased to 90.43% ee and the chemical purity decreased to 97.97%.

Comparative Example 14

A sample of (S)-2-methoxycyclohexanone (the same one as in Example 19) was diluted with an aqueous solution containing an inorganic salt, acid, or base to give a 50 wt % solution. The solution was sealed in a glass ample, with the atmosphere therein replaced with argon. The ample was heated at 80° C. for 65 hours. The ample was opened and the content was tested for optical purity and chemical purity. The results are shown in Table 7.

TABLE 7

| Inorganic compound | Optical purity (% ee) | Chemical purity (%) |
|---|---|---|
| Sodium hydrogensulfite (0.2 eq) | 95.53 | 96.65 |
| Sodium sulfite (saturated aq. solution) | 95.21 | 97.80 |
| Sodium chloride (saturated aq. solution) | 92.76 | 98.80 |
| 1N sodium hydroxide | 0.00 | 64.34 |
| 1N sulfuric acid | 0.00 | not detected |
| Hydrochloric acid (0.07 eq) | 0.00 | 17.36 |

(Stabilization by inorganic oxide)

Example 25

A 50-ml stoppered test tube was charged with 10 g of (S)-2-methoxycyclohexanone (having an optical purity of 98.7% ee and a chemical purity of 99.2%). The sample was incorporated with 1 g of "Zeoram A-5" (made by Toso) which had previously been dried at 100° C. for 5 hours under reduced pressure. With the atmosphere in the test tube replaced with argon, the sample was stirred at room temperature for 1 hour and allowed to stand at 20–25° C. for 7 days. The sample remained almost unchanged in optical purity (98.5% ee) and chemical purity (99.2%). By contrast, the sample without "Zeoram A-5" decreased in optical purity to 96.5% ee although it remained unchanged in chemical purity (99.2%).

Example 26

A 500-ml four-mouth flask equipped with a thermometer, dropping funnel, condenser, and stirrer was charged with 13.0 g (0.1 mol) of (S)-2-methoxycyclohexanol having an optical purity of 99.8% ee, 7 g of dichloromethane, and 30 g of 10% aqueous solution of sulfuric acid (30 mmol). The reactants were stirred at 20–25° C. The flask was further charged with 60 g of aqueous solution of sodium hypochlorite containing 12.1% effective chlorine over about 1 hour. Stirring was continued for 30 minutes. The reaction solution was analyzed by gas chromatography to confirm that the peak due to (S)-2-methoxycyclohexanol had disappeared. The reaction solution was given 2 g of sodium hydrogensulfite with stirring. It was confirmed that the reaction solution did not change potassium iodide starch paper into purple any longer. The reaction solution was given 30 ml of 10% aqueous solution of sodium carbonate, followed by stirring at 20–25° C. for 1 hour. The reaction solution was extracted twice with 50 g of dichloromethane. The dichloromethane layers were combined together and washed with saturated aqueous solution of sodium chloride. Upon concentration, there was obtained 21.6 g of dichloromethane solution containing 11.5 g (90 mmol) of (S)-2-methoxycyclohexanone, which has an optical purity of 99.6% ee. This solution (10 g) was placed in a test tube and incorporated with 1 g of "Zeoram A-5", which had previously been dried at 100° C. for 5 hours under reduced pressure, in the same manner as in Example 25. With the atmosphere in the test tube replaced with argon, the sample was stirred at room temperature for 1 hour and allowed to stand at 20–25° C. for 7 days. The sample was found to have an optical purity of 98.6% ee. By contrast, the sample without "Zeoram A-5" decreased in optical purity to 76.1% ee.

Example 27

The same procedure as in Example 26 was repeated except that diethyl ether was used for extraction. There was obtained 20.9 g of concentrated solution which contained 9.8 g of (S)-2-methoxycyclohexanone having an optical purity of 99.6% ee. This solution (10 g) was placed in a test tube and incorporated with 3 g of "Wakogel C-200" (made by Wako Pure Chemical Industries, Ltd.), which had previously been dried at 100° C. for 5 hours under reduced pressure, in the same manner as in Example 25. With the atmosphere in the test tube replaced with argon, the sample was stirred at room temperature for 1 hour and allowed to stand at 20–25° C. for 7 days. The sample was found to have an optical purity of 99.0% ee. No peaks due to impurities were detected in gas chromatography. By contrast, the sample without "Wakogel C-200" decreased in optical purity to 89.3% ee.

Example 28

The same procedure as in Example 27 was repeated to give 23.5 g of concentrated solution which contained 9.6 g of (S)-2-methoxycyclohexanone having an optical purity of 99.6% ee. This solution (10 g) was placed in a test tube and incorporated with 3 g of "Wakogel C-200", which had previously been dried at 100° C. for 5 hours under reduced pressure, in the same manner as in Example 25. With the atmosphere in the test tube replaced with argon, the sample was stirred at room temperature for 1 hour and allowed to stand at 20–25° C. for 7 days. The sample was found to have an optical purity of 98.7% ee. A few peaks due to impurities were detected in gas chromatography, although they were not detected at the time of charging. By contrast, the sample without "Wakogel C-200" decreased in optical purity to 89.0% ee. More peaks due to impurities were detected in gas chromatography, although they were not detected at the time of charging.

Example 29

The same procedure as in Example 26 was repeated except that dichloroethane was used for extraction. There was obtained 21.9 g of concentrated solution which contained 12.0 g of (S)-2-methoxycyclohexanone having an optical purity of 95.9% ee. This solution (8 g) was placed in a test tube and incorporated with 2 g of "Zeoram A-5", which had previously been dried at 100° C. for 5 hours under reduced pressure, in the same manner as in Example 25. With the atmosphere in the test tube replaced with argon, the sample was stirred at room temperature for 1 hour and allowed to stand at 40° C. for 13 hours. The sample was found to have an optical purity of 95.9% ee. No peaks due to impurities were detected in gas chromatography. By contrast, the sample without "Zeoram A-5" decreased in optical purity to 87.1% ee.

Example 30

The concentrated solution (10 g) obtained in Example 29 was diluted with 20 g of dichloroethane. The diluted solution was passed through a column filled with "Zeoram A-5" (10 g), which had previously been dried at 100° C. for 5 hours under reduced pressure. The filtrate was allowed to stand at 40° C. for 13 hours in a container, with the atmosphere therein replaced with argon. The sample was found to have an optical purity of 95.7% ee. No peaks due to impurities were detected in gas chromatography.

Exploitation in Industry

The present invention provides an optically active amino acid ester, an optically active alcohol, and an optically active ketone, which are useful as an intermediate for medicines and agricultural chemicals.

What is claimed is:

1. A process for producing an optically active amino acid ester, said process comprising reacting a racemic alcohol with an optically active amino acid to produce an amino acid ester, and performing diastereomer resolution thereon, wherein said optically active amino acid is at least one acid selected from the group consisting of an optically active α-amino acid and an N-substituted amino acid and wherein said diastereomer resolution is performed by a process selected from the group consisting of crystallization separation, column separation, and simulated moving bed separation.

2. A process defined in claim 1, wherein the optically active amino acid is selected from the group consisting of the formulas (I), (II), (III), and (IV):

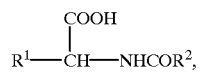

(I)

where

R¹ denotes:
(i) an unsubstituted or substituted $C_{1-10}$ alkyl group, with the substituent being a hydroxyl group, carboxyl group, or carbamyl group; or
(ii) an unsubstituted or substituted aryl group, with the substituent being a $C_{1-10}$ alkyl group, $C_{1-10}$ alkoxyl group, or hydroxyl group; or
(iii) an unsubstituted or substituted aralkyl group, with the substituent on the aromatic ring being a $C_{1-10}$ alkyl group, $C_{1-10}$ alkoxyl group, or hydroxyl group; and R² denotes:
(i) a hydrogen atom;
(ii) a $C_{1-10}$ alkyl group;
(iii) an unsubstituted or substituted aryl group, with the substituent being a $C_{1-10}$ alkyl group, $C_{1-10}$ alkoxyl group, nitro group, or halogen; or
(iv) an unsubstituted or substituted aralkyl group, with the substituent on the aromatic ring being a $C_{1-10}$ alkyl group, $C_{1-10}$ alkoxyl group, or halogen; or
(v) an unsubstituted or substituted aralkyloxy group, with the substituent on the aromatic ring being a $C_{1-10}$ alkyl group, $C_{1-10}$ alkoxyl group, or halogen;

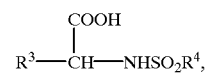

(II)

where

R³ denotes:
(i) an unsubstituted or substituted $C_{1-10}$ alkyl group, with the substituent being a hydroxyl group, carboxyl group, or carbamyl group; or
(ii) an unsubstituted or substituted aryl group, with the substituent being a $C_{1-10}$ alkyl group, $C_{1-10}$ alkoxyl group, or hydroxyl group; or
(iii) an unsubstituted or substituted aralkyl group, with the substituent on the aromatic ring being a $C_{1-10}$ alkyl group, a $C_{1-10}$ alkoxyl group, or a hydroxyl group; and R⁴ denotes:
(i) a $C_{1-10}$ alkyl group; or
(ii) an unsubstituted or substituted aryl group, with the substituent being a $C_{1-10}$ alkyl group, or a $C_{1-10}$ alkoxyl group, or a nitro group, or halogen; or
(iii) an unsubstituted or substituted aralkyl group, with the substituent on the aromatic ring being a $C_{1-10}$ alkyl group, or a $C_{1-10}$ alkoxyl group, or halogen;

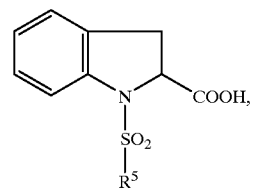

(III)

where

R⁵ denotes:
(i) a $C_{1-10}$ alkyl group; or
(ii) an unsubstituted or substituted aryl group, with the substituent being a $C_{1-10}$ alkyl group, or a $C_{1-10}$ alkoxyl group, nitro group, or halogen; or
(iii) an unsubstituted or substituted aralkyl group, with the substituent on the aromatic ring being a $C_{1-10}$ alkyl group, or $C_{1-10}$ alkoxyl group, or halogen; and (IV)

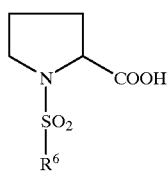

where

R⁶ denotes:
(i) $C_{1-10}$ alkyl group; or
(ii) an unsubstituted or substituted aryl group, with the substituent being a $C_{1-10}$ alkyl group, or $C_{1-10}$ alkoxyl group, nitro group, or halogen; or
(iii) an unsubstituted or substituted aralkyl group, with the substituent on the aromatic ring being a $C_{1-10}$ alkyl group, or a $C_{1-10}$ alkoxyl group, or halogen.

3. A process defined in claim 1, wherein said racemic alcohol is a secondary alcohol.

4. A process defined in claim 1, wherein said racemic alcohol is an alicyclic alcohol or a heteroalicyclic alcohol.

5. An optically active amino acid ester produced by the process of claim 1 wherein said optically active amino acid ester has an optical purity higher than 50% ee.

6. An optically active amino active amino acid ester as defined in claim 5, wherein said optical purity of said optically active amino acid ester is higher than 80% ee.

7. An optically active ester as defined in claim 5 or claim 6, wherein said optically active ester is represented by a formula selected from the group consisting of (V), (VI), (VII), and (VIII):

(V)

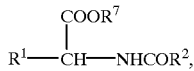

where

R¹ denotes:
(i) an unsubstituted or substituted $C_{1-10}$ alkyl group, with the substituent being a hydroxyl group, carboxyl group, or carbamyl group;
(ii) an unsubstituted or substituted aryl group, with the substituent being a $C_{1-10}$ alkyl group, a $C_{1-10}$ alkoxyl group, or a hydroxyl group; or
(iii) an unsubstituted or substituted aralkyl group, having a substituent on the aromatic ring being a $C_{1-10}$ alkyl group, a $C_{1-10}$ alkoxyl group, or a hydroxyl group; and R² denotes:
(i) a hydrogen atom;
(ii) a $C_{1-10}$ alkyl group;
(iii) an unsubstituted or substituted aryl group, with the substituent being a $C_{1-10}$ alkyl group, a $C_{1-10}$ alkoxyl group, nitro group, or halogen;
(iv) an unsubstituted or substituted aralkyl group, with the substituent on the aromatic ring being a $C_{1-10}$ alkyl group, a $C_{1-10}$ alkoxyl group, or halogen; or
(v) an unsubstituted or substituted aralkyloxy group, with the substituent on the aromatic ring being a $C_{1-10}$ alkyl group, a $C_{1-10}$ alkoxyl group, or halogen; and wherein (VI)

$$R^3—\underset{\underset{\text{CH}}{|}}{\text{COOR}^7}—NHSO_2R^4,$$

where

R³ denotes:
(i) an unsubstituted or substituted $C_{1-10}$ alkyl group, with the substituent being a hydroxyl group, carboxyl group, or a carbamyl group;
(ii) an unsubstituted or substituted aryl group, with the substituent being a $C_{1-10}$ alkyl group, a $C_{1-10}$ alkoxyl group, or a hydroxyl group; or
(iii) an unsubstituted or substituted aralkyl group, with the substituent on the aromatic ring being a $C_{1-10}$ alkyl group, a $C_{1-10}$ alkoxyl group, or a hydroxyl group; and R⁴ denotes:
(i) a $C_{1-10}$ alkyl group;
(ii) an unsubstituted or substituted aryl group, with the substituent being a $C_{1-10}$ alkyl group, a $C_{1-10}$ alkoxyl group, nitro group, or a halogen; or
(iii) an unsubstituted or substituted aralkyl group, with the substituent on the aromatic ring being a $C_{1-10}$ alkyl group, a $C_{1-10}$ alkoxyl group, or a halogen; and (VIII)

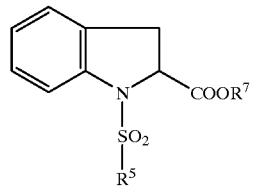

where

R₅ denotes:
(i) a $C_{1-10}$ alkyl group;
(ii) an unsubstituted or substituted aryl group, with the substituent being a $C_{1-10}$ alkyl group, a $C_{1-10}$ alkoxyl group, a nitro group, or a halogen; or
(iii) an unsubstituted or substituted aralkyl group, with the substituent on the aromatic ring being a $C_{1-10}$ alkyl group, a $C_{1-10}$ alkoxyl group, or a halogen; and R⁷ denotes a residue of alcohol selected from the group consisting of secondary alcohols, alicyclic alcohols, and heteroalicyclic alcohols;

(VIII)

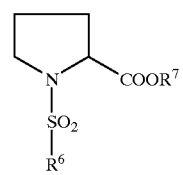

where

R⁶ denotes:
(i) a $C_{1-10}$ alkyl group;
(ii) an unsubstituted or substituted aryl group, with the substituent being a $C_{1-10}$ alkyl group, a $C_{1-10}$ alkoxyl group, nitro group, or a halogen; or
(iii) an unsubstituted or substituted aralkyl group, with the substituent on the aromatic ring being a $C_{1-10}$ alkyl group, a $C_{1-10}$ alkoxyl group, or a halogen; and $R^7$ denotes a residue of alcohol selected from the group consisting of secondary alcohols, alicyclic alcohols, and heteroalicyclic alcohols.

8. A process for producing an optically active alcohol comprising hydrolyzing the optically active amino acid ester obtained in claim 1 or the optically active amino acid ester obtained in claim 5.

9. A process for preparing a tartaric acid ester, comprising reacting a racemic secondary alcohol with an optically active tartaric acid derivative anhydride represented by the formula (IX) below,

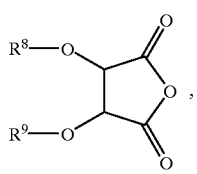
(IX)

where $R^8$ and $R^9$ are identical or different, each being selected from the group consisting of a $C_{1-4}$ alkyl group, alkoxyl group, phenyl group, $C_{1-4}$ alkylcarbonyl group, unsubstituted arylcarbonyl group, and an arylcarbonyl group substituted with a $C_{1-4}$ alkyl group or halogen atom; and wherein the tartaric acid skeleton is of (R,R) conformation or (S,S) conformation, said racemic secondary alcohol being represented by the formula (X) below

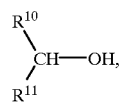
(X)

where $R^{10}$ and $R^{11}$ are different, each being selected from the group consisting of an unsubstituted or substituted $C_{1-4}$ alkyl group, an unsubstituted or substituted phenyl group, with the substituent being a $C_{1-4}$ alkyl group, or a halogen atom, and an aralkyl group; and wherein $R^{10}$ and $R^{11}$ may combine to form an alicyclic alkyl group substituted by a $C_{1-4}$ alkyl group or an alkoxyl group, thereby producing a tartaric acid ester represented by the formula (XI) below,

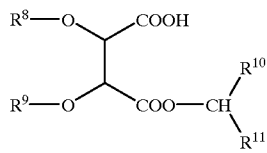
(XI)

where $R^8$, $R^9$, $R^{10}$, and $R^{11}$ are defined as above,
further characterized in that said reaction is carried out in the presence of a Lewis acid.

10. A process for producing a tartaric acid ester as defined in claim 9, wherein said optically active tartaric acid derivative anhydride is at least one anhydride selected from the group consisting of an optically active O,O-diacyltartaric acid anhydrides represented by the formula (XII) below

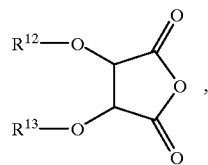
(XII)

where $R^{12}$ and $R^{13}$ are identical or different, each denoting a $C_{1-4}$ alkylcarbonyl group; and wherein the tartaric acid skeleton is of (R,R) conformation or (S,S) conformation.

11. A process for producing a tartaric acid ester as defined in claim 9, wherein said optically active tartaric acid derivative anhydride is represented by the formula (XIII) below

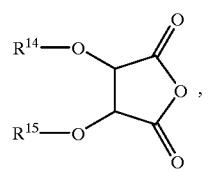
(XIII)

where $R^{14}$ and $R^{15}$ are identical or different, each denoting an unsubstituted or substituted arylcarbonyl group, with the substituent being a $C_{1-4}$ alkyl group or halogen atom; and the tartaric acid skeleton is of (R,R) conformation or (S,S) conformation.

12. A process for producing a tartaric acid ester as defined in claim 9, wherein said racemic secondary alcohol is a racemic alicyclic alcohol derivative.

13. A process for producing a tartaric acid ester, comprising reacting a racemic secondary alcohol with an optically active tartaric acid derivative anhydride represented by the formula (IX),

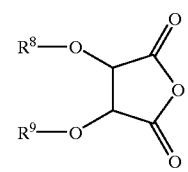
(IX)

where $R^8$ and $R^9$ are identical or different, each being selected from the group consisting of a $C_{1-4}$ alkyl group, alkoxyl group, phenyl group, $C_{1-4}$ alkylcarbonyl group, unsubstituted arylcarbonyl group, and an arylcarbonyl group substituted with a $C_{1-4}$ alkyl group or halogen atom; and wherein the tartaric acid skeleton is on (R,R) conformation or (S,S) conformation, said racemic secondary alcohol being represented by the formula (X)

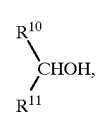
(X)

where $R^{10}$ and $R^{11}$ are different, each being selected from the group consisting of an unsubstituted or substituted $C_{1-4}$ alkyl group, an unsubstituted or substituted phenyl group, with the substituent being a $C_{1-4}$ alkyl group, or a halogen atom, and an aralkyl group; and wherein $R^{10}$ and $R^{11}$ may combine to form an alicyclic alkyl group substituted by a $C_{1-4}$ alkyl group or an alkoxyl group, thereby producing a tartaric acid ester represented by the formula (XI),

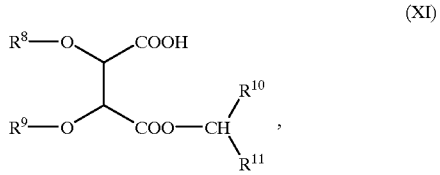

(XI)

where $R^8$, $R^9$, $R^{10}$ and $R^{11}$ are defined as above, wherein said racemic secondary alcohol is 2-methoxycyclohexanol, further characterized in that said reaction is carried out in the presence of a Lewis acid.

14. A process for producing a tartaric acid ester comprising reacting a racemic secondary alcohol with an optically active tartaric acid derivative anhydride represented by the formula (IX),

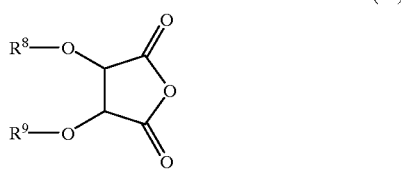

(IX)

where $R^8$ and $R^9$ are identical or different, each being selected from the group consisting of a $C_{1-4}$ alkyl group, alkoxyl group, phenyl group, $C_{1-4}$ alkylcarbonyl group, unsubstituted or substituted arylcarbonyl group, and an arylcarbonyl group substituted with a $C_{1-4}$ alkyl group or halogen atom; and wherein the tartaric acid skeleton is of (R,R) conformation or (S,S) conformation, said racemic secondary alcohol being represented by the formula (X)

(X)

where $R^{10}$ and $R^{11}$ are different, each being selected from the group consisting of an unsubstituted or substituted $C_{1-4}$ alkyl group, an unsubstituted or substituted phenyl group, with the substituent being a $C_{1-4}$ alkyl group, or a halogen atom, and an aralkyl group; and wherein $R^{10}$ and $R^{11}$ may combine to form an alicyclic alkyl group substituted by a $C_{1-4}$ alkyl group or an alkoxyl group, thereby producing a tartaric acid ester represented by the formula (XI),

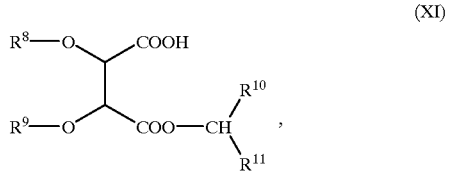

(XI)

where $R^8$, $R^9$, $R^{10}$ and $R^{11}$ are defined as above, further characterized in that said reaction is carried out in the presence of a Lewis acid, wherein said Lewis acid is an iron chloride.

15. A process for producing an optically active tartaric acid ester, said process comprising performing diastereomer resolution on a tartaric acid ester represented by the formula (XI) below

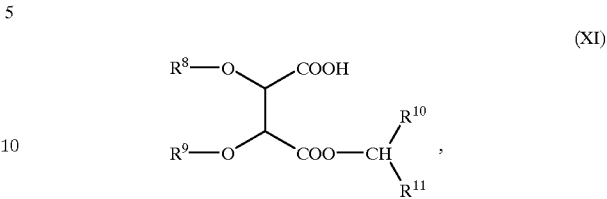

(XI)

where $R^8$ and $R^9$ are identical or different, each being selected from the group consisting of a $C_{1-4}$ alkyl group, an alkoxyl group, a phenyl group, a $C_{1-4}$ alkylcarbonyl group, or an unsubstituted or substituted arylcarbonyl group with the substituent being a $C_{1-4}$ alkyl group and a halogen atom; $R^{10}$ and $R^{11}$ are different, each being selected from the group consisting of an unsubstituted or substituted $C_{1-4}$ alkyl group, an unsubstituted or substituted phenyl group, with the substituent being a $C_{1-4}$ alkyl group or halogen atom, and an aralkyl group; and wherein $R^{10}$ and $R^{11}$ may combine to form an alicyclic alkyl group substituted by a $C_{1-4}$ alkyl group or alkoxyl group, said diastereomer resolution is performed by a process selected from the group consisting of crystallization separation, column separation and simulated moving bed separation.

16. A process for producing an optically active tartaric acid ester, said process comprising performing diastereomer resolution on the tartaric acid ester produced by the process defined in claim 9.

17. A tartaric acid ester represented by the formula (XIV) below

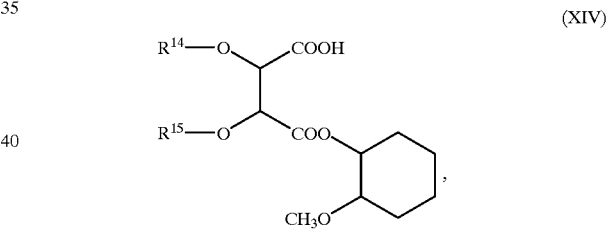

(XIV)

where $R^{14}$ and $R^{15}$ are identical or different, each denoting a hydrogen atom, or a $C_{1-4}$ alkyl group, or a halogen-substituted arylcarbonyl group.

18. A tartaric acid ester having an optical purity higher than 80% ee, which is represented by the formula (XIV) below

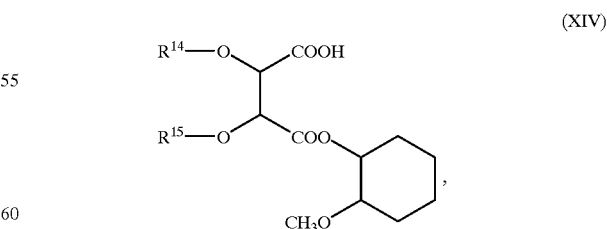

(XIV)

where $R^{14}$ and $R^{15}$ are identical or different, each denoting a hydrogen atom, or a $C_{1-4}$ alkyl group, or a halogen-substituted arylcarbonyl group.

19. A process for producing an optically active alcohol, said process comprising hydrolyzing an optically active tartaric acid ester produced by the process defined in claim 15 or the optically active tartaric acid ester defined in claim 18.

20. A process for producing an optically active ketone, comprising reacting a secondary alcohol with an alkali metal hypohalite or alkaline earth metal hypohalite in an aqueous medium, wherein said reaction is carried out in the presence of an aliphatic compound having a partition ratio greater than 1 in water at 20° C. for an alicyclic alcohol as the starting material and further having a solubility that is lower than 5 wt % in water at 40° C., and also in the presence of a mineral acid having a pH less than 3 in an amount of 0.1–2 equivalents for said alicyclic alcohol.

21. A process for producing an optically active ketone according to claim 20, wherein said optically active ketone is an alicyclic ketone, wherein said secondary alcohol is an alicyclic alcohol represented by the formula (XV) below

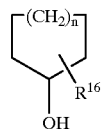

(XV)

where $R^{16}$ denotes a $C_{1-4}$ alkyl group or a $C_{1-4}$ alkoxyl group which is not connected to that carbon atom to which the hydroxyl group is connected, and wherein n is an integer of 0–3 and wherein said ketone is represented by the formula (XVI) below

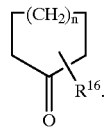

(XVI)

22. A process as defined in claim 21, wherein said alicyclic alcohol is an optically active alicyclic alcohol.

23. A process as defined in claim 21, wherein said alicyclic alcohol is a cyclohexanol derivative represented by the formula (XVII) below

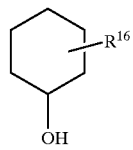

(XVII)

where $R^{16}$ denotes a $C_{1-4}$ alkyl group or a $C_{1-4}$ alkoxyl group which is not connected to that carbon atom to which the hydroxyl group is connected, and wherein said alicyclic ketone is a cyclohexanone derivative represented by the formula (XVIII) below

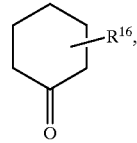

(XVIII)

where $R^{16}$ denotes a $C_{1-4}$ alkyl group or a $C_{1-4}$ alkoxyl group.

24. A process as defined in claim 23, wherein said alicyclic alcohol is 2-methoxycyclohexanol, and wherein said alicyclic ketone is 2-methoxycyclohexanone.

25. A process as defined in claim 21, wherein said aliphatic compound present in the reaction system is an aliphatic halogen compound.

26. A process as defined in claim 25, wherein said aliphatic halogen compound is an alkyl chloride or alkyl bromide.

27. A process as defined in claim 26, wherein said alkyl chloride is selected from the group consisting of dichloromethane, chloroform, tetrachloromethane, monochloromethane, 1,1-dichloroethane, 1,2-dichloroethane, and 1,1,1-trichloroethane.

28. A process for producing an alicyclic ketone as defined in claim 21, wherein said mineral acid is sulfuric acid, hydrochloric acid, or phosphoric acid.

29. A process for producing an optically active ketone comprising reacting an optically active alicyclic alcohol represented by the formula (XIX) below

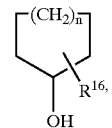

(XIX)

where $R^{16}$ denotes a $C_{1-4}$ alkyl group or a $C_{1-4}$ alkoxyl group which is not connected to that carbon atom to which the hydroxyl group is connected, and n is an integer of 0–3, with an alkali metal hypohalite or alkaline earth metal hypohalite in an acid aqueous solution, thereby producing an optically active alicyclic ketone represented by the formula (XX) below

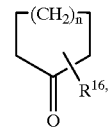

(XX)

where $R^{16}$ denotes a $C_{1-4}$ alkyl group or a $C_{1-4}$ alkoxyl group, and n is an integer of 2–5, rendering said reaction solution basic after the completion of said reaction, thereby producing a stable, optically active alicyclic ketone represented by the formula (XXI) below

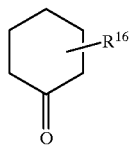

(XXI)

where $R^{16}$ denotes a $C_{1-4}$ alkyl group or $C_{1-4}$ alkoxyl group, and n is an integer of 2–5.

30. A process for producing a stable, optically active alicyclic ketone as defined in claim 29, wherein said optically active alicyclic alcohol is produced by the process defined in claim 8.

31. A process for producing an optically active alicyclic ketone as defined in claim 29, wherein said optically active alicyclic alcohol is a cyclohexanol derivative represented by the formula (XXII) below

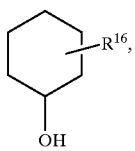

(XXII)

where $R^{16}$ denotes a $C_{1-4}$ alkyl group or $C_{1-4}$ alkoxyl group, and the substituent is connected to the 2- or 3-position, and wherein the optically active alicyclic ketone is a cyclohexanone derivative represented by the formula (XXIII) below

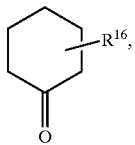

(XXIII)

where $R^{16}$ denotes a $C_{1-4}$ alkyl group or a $C_{1-4}$ alkoxyl group, an the substituent is connected to the 2- or 3-position.

32. A process for producing an optically active alicyclic ketone as defined in claim 31, wherein an optically active alicyclic alcohol is 2-methoxycyclohexanol and said optically active alicyclic ketone is 2-methoxycyclohexanone.

33. A process for producing a stable, optically active alicyclic ketone as define in claim 29, wherein the reaction solution is made basic in the range of pH 7.1–10.

34. A process for producing an optically active alicyclic ketone as defined in claim 33, wherein the reaction solution is kept basic for 0.01–5 hours at 0–40° C.

35. A process for producing a stable, optically active alicyclic ketone as defined in claim 22, wherein the reaction solution is made basic after the completion of the reaction.

36. A method for storing an optically active α-ketone which comprises the step of keeping the halogen ion content in the optically active α-substituted ketone below 500 ppm when measured by potentiometric titration after heating under reflux with 1N aqueous solution of sodium hydroxide.

37. A method for storing an optically active α-ketone which comprises keeping the optically active α-substituted ketone away from oxygen, metal, an acid, or a base.

38. A method for storing an optically active α-substituted ketone as defined in claim 36, wherein the optically active α-substituted ketone is an optically active α-substituted cyclic ketone represented by the formula (XXIV) below

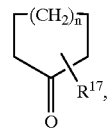

(XXIV)

where $R^{17}$ denotes a $C_{1-8}$ alkoxyl group or alkyl group, and n is an integer of 0–3, and is stored in an environment that is free of halogens.

39. A method for storing an optically active α-substituted cyclic ketone as defined in claim 36, wherein said compound is stored together with a halogen-free solvent.

40. A method for storing an optically active α-substituted cyclic ketone as defined in claim 39, wherein said halogen-free solvent is a hydrocarbon, ether, or ketone.

41. A method for storing an optically active α-substituted cyclic ketone as defined in claim 39, wherein said compound has a concentration ranging from 10 to 99 wt %.

42. A method for storing an optically active α-substituted cyclic ketone as define in claim 36, wherein said compound is stored in an atmosphere of inert gas.

43. A method for storing an optically active α-substituted cyclic ketone as defined in claim 42, wherein said inert gas is nitrogen, helium, or argon.

44. A method for storing an optically active α-substituted cyclic ketone as defined in claim 37, wherein said metal is selected from the group consisting of iron, manganese, nickel, copper, zinc, and alloy thereof.

45. A method for storing an optically active α-substituted cyclic ketone as defined in claim 36, wherein said compound is an optically active 2-methoxycyclohexanone.

46. A method for stabilizing an optically active α-substituted ketone which comprises bringing an optically active α-substituted ketone represented by the formula (XXV) below into contact with an inorganic oxide compound, wherein said optically active α-ketone has the formula:

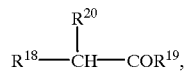

(XXV)

where
$R^{18}$ and $R^{19}$ each denote:
  (i) a $C_{1-8}$ aralkyl group;
  (ii) an identical or different unsubstituted or substituted $C_{6-12}$ aryl group or aralkyl group, with the substituent being a $C_{1-4}$ alkyl group, alkoxyl group, or halogen; $R^{18}$ and $R^{19}$ may combine together to form an alkyl ring; and wherein $R^{20}$ denotes a $C_{1-4}$ alkyl group, alkoxyl group, or halogen.

47. A method for stabilizing an optically active α-substituted ketone as defined in claim 46, wherein said inorganic oxide is a substance capable of adsorbing polar compounds.

48. A method for stabilizing an optically active α-substituted ketone as defined in claim 46, wherein said inorganic compound is zeolite or silica gel.

49. A method for stabilizing an optically active α-substituted ketone as defined in claim 46, wherein the optically active α-substituted ketone is one which is produced by oxidizing an optically active α-substituted alcohol with halogen, halogenic acid, hypohalous acid, or a source generating hypohalous acid.

50. A method for stabilizing an optically active α-substituted ketone as defined in claim 46, wherein said compound is an optically active α-substituted alicyclic ketone.

51. A method for stabilizing an optically active α-substituted ketone as defined in claim 50, wherein the optically active α-substituted alicyclic ketone is optically active α-methoxycyclohexanone.

52. A method for stabilizing an optically active α-substituted ketone as defined in claim 51, wherein the optically active α-methoxycyclohexanone is one which is produced by oxidizing optically active α-methoxycyclohexanol with hypohalous acid or a source generating hypohalous acid.

53. A method for stabilizing an optically active α-substituted ketone as defined in claim 46, wherein said compound is stored in an atmosphere of inert gas.

54. A method for stabilizing an optically active α-substituted ketone as defined in claim 53, wherein the inert gas is nitrogen, helium, or argon.

* * * * *

UNITED STATES PATENT AND TRADEMARK OFFICE
CERTIFICATE OF CORRECTION

PATENT NO.    : 6,320,069 B1
DATED         : November 20, 2001
INVENTOR(S)   : Sato et al.

It is certified that error appears in the above-identified patent and that said Letters Patent is hereby corrected as shown below:

<u>Column 3,</u>
Line 60, please change "a id" to -- acid --.

<u>Column 4,</u>
Line 9, please insert the following paragraph after "D-tartaric acid.":
-- The racemic secondary alcohol (as another raw material) include, for example, alkyl secondary alcohol (such as methylethyl alcohol), aralkyl alcohol (such as α-phenylethyl alcohol), and alicyclic alcohol (such as 2-methoxycyclohexanol). The racemic alcohol includes not only a mixture of R-form and S-form in equal amounts but also a mixture containing S-form or R-form in an amount more than 50% and less than 99%. --

<u>Column 7,</u>
Line 44, please change "decompose" to -- decomposed --.

<u>Column 33,</u>
Line 46, please change "an" to -- said --.

Signed and Sealed this

Tenth Day of September, 2002

Attest:

JAMES E. ROGAN
*Director of the United States Patent and Trademark Office*

*Attesting Officer*